United States Patent
Snell et al.

(10) Patent No.: US 10,308,568 B2
(45) Date of Patent: Jun. 4, 2019

(54) SELECTIVE POISONING OF AROMATIZATION CATALYSTS TO INCREASE CATALYST ACTIVITY AND SELECTIVITY

(71) Applicant: Chevron Phillips Chemical Company LP, The Woodlands, TX (US)

(72) Inventors: Ryan W. Snell, Kingwood, TX (US); Theresa E. Feltes, Kingwood, TX (US); Cori A. Demmelmaier-Chang, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/582,798

(22) Filed: May 1, 2017

(65) Prior Publication Data

US 2018/0312452 A1    Nov. 1, 2018

(51) Int. Cl.
| | | |
|---|---|---|
| C07C 5/32 | (2006.01) | |
| C07C 5/00 | (2006.01) | |
| C10G 35/09 | (2006.01) | |
| C10G 59/02 | (2006.01) | |
| C07C 5/41 | (2006.01) | |
| B01J 8/04 | (2006.01) | |
| C10G 35/095 | (2006.01) | |
| B01J 8/02 | (2006.01) | |

(52) U.S. Cl.
CPC .............. *C07C 5/417* (2013.01); *B01J 8/0214* (2013.01); *B01J 8/0411* (2013.01); *B01J 8/0419* (2013.01); *C10G 35/09* (2013.01); *C10G 35/095* (2013.01); *C10G 59/02* (2013.01); *B01J 2208/025* (2013.01); *C07C 2529/62* (2013.01)

(58) Field of Classification Search
CPC .. C07C 5/41; C07C 5/32; C07C 5/321; C07C 5/322; C07C 5/00
See application file for complete search history.

(56) References Cited

U.S. PATENT DOCUMENTS

| | | | |
|---|---|---|---|
| 2,479,110 A * | 8/1949 | Haensel | B01J 27/13 208/139 |
| 4,456,527 A | 6/1984 | Buss et al. | |
| 5,196,631 A | 3/1993 | Murakawa et al. | |
| 5,389,235 A | 2/1995 | Russ et al. | |
| 5,401,365 A | 3/1995 | Chen et al. | |
| 5,401,386 A | 3/1995 | Morrison et al. | |
| 5,866,743 A | 2/1999 | Heyse et al. | |
| 6,190,539 B1 * | 2/2001 | Holtermann | B01J 29/064 208/135 |
| 6,207,042 B1 | 3/2001 | Holtermann et al. | |
| 6,406,614 B1 | 6/2002 | Tiedtke et al. | |

(Continued)

FOREIGN PATENT DOCUMENTS

WO    WO 2013/134385    9/2013

OTHER PUBLICATIONS

Rahimpour et al. (Progress in catalytic naphtha reforming process: A review, Applied Energy 109 (2013) pp. 79-93. (Year: 2013).*

*Primary Examiner* — Youngsul Jeong
(74) *Attorney, Agent, or Firm* — Merchant & Gould P.C.

(57) ABSTRACT

Spent aromatization catalysts containing a transition metal and a catalyst support are selectively poisoned in the disclosed reforming methods, resulting in improvements in overall aromatics yield and selectivity.

20 Claims, 8 Drawing Sheets

(56) References Cited

U.S. PATENT DOCUMENTS

| | | |
|---|---|---|
| 6,518,470 B1 | 2/2003 | Fukunaga et al. |
| 6,548,030 B2 | 4/2003 | Heyse et al. |
| 6,812,180 B2 | 11/2004 | Fukunaga |
| 7,153,801 B2 | 12/2006 | Wu |
| 7,544,335 B2 | 6/2009 | Scanlon et al. |
| 7,582,272 B2 | 9/2009 | Glova et al. |
| 7,932,425 B2 | 4/2011 | Blessing et al. |
| 8,119,203 B2 | 2/2012 | Hise et al. |
| 8,835,341 B2 | 9/2014 | Khare |
| 9,085,736 B2 | 7/2015 | Morrison et al. |
| 9,382,175 B2 | 7/2016 | Khare |
| 9,387,467 B2 | 7/2016 | Khare |

\* cited by examiner

SELECTIVE POISONING OF AROMATIZATION CATALYSTS TO INCREASE CATALYST ACTIVITY AND SELECTIVITY

FIELD OF THE INVENTION

The present disclosure concerns catalytic reforming methods and related aromatization reactor vessels, and more particularly relates to the selective poisoning of aromatization catalysts containing a transition metal and a catalyst support in order to increase catalyst activity and selectivity.

BACKGROUND OF THE INVENTION

The catalytic conversion of non-aromatic hydrocarbons into aromatic compounds, often referred to as aromatization or reforming, is an important industrial process that can be used to produce benzene, toluene, xylenes, and the like. The aromatization or reforming process often is conducted in a reactor system that can contain one or more reactors containing transition metal based catalysts. These catalysts can provide increased selectivity to and/or increased yield of the desired aromatic compounds. However, under commercial reaction conditions, these catalysts slowly lose their activity, often simultaneously with a loss of selectivity to the desired aromatic compounds. Such catalysts are often referred to as "spent" catalysts once economic or operational thresholds are passed.

Despite the existence of spent catalysts in an aromatization reactor, it would be beneficial to continue to operate the aromatization reactor, in part due to the expense incurred with unplanned production shutdowns, as well as the cost to remove and replace the spent catalyst with fresh catalyst. Accordingly, it is to these ends that the present disclosure is generally directed.

SUMMARY OF THE INVENTION

Methods for reforming hydrocarbons are disclosed and describe herein. One such reforming method can comprise (a) providing a radial flow reactor comprising a catalyst bed, the catalyst bed comprising an outer reforming zone and an inner reforming zone, wherein the outer reforming zone comprises a spent first aromatization catalyst comprising a first transition metal and a first catalyst support, and the inner reforming zone comprises a second aromatization catalyst comprising a second transition metal and a second catalyst support; (b) introducing a catalyst poisoning agent into the radial flow reactor and contacting at least a portion of the spent first aromatization catalyst in the outer reforming zone; and (c) introducing a hydrocarbon feed into the radial flow reactor comprising the catalyst bed, and contacting the hydrocarbon feed with the catalyst bed under reforming conditions to produce an aromatic product.

Another reforming method consistent with this disclosure can comprise (A) introducing a first hydrocarbon feed into a radial flow reactor comprising a catalyst bed, and contacting the first hydrocarbon feed with the catalyst bed under first reforming conditions to produce a first aromatic product, wherein the catalyst bed comprises an outer reforming zone and an inner reforming zone, the outer reforming zone comprises a first aromatization catalyst comprising a first transition metal and a first catalyst support, and the inner reforming zone comprises a second aromatization catalyst comprising a second transition metal and second catalyst support; (B) performing step (A) for a time period sufficient to form a spent first aromatization catalyst in the outer reforming zone; (C) introducing a catalyst poisoning agent into the radial flow reactor and contacting at least a portion of the spent first aromatization catalyst in the outer reforming zone; and (D) introducing a second hydrocarbon feed into the radial flow reactor comprising the catalyst bed, and contacting the second hydrocarbon feed with the catalyst bed under second reforming conditions to produce a second aromatic product.

Also disclosed herein are aromatization reactor vessels and reactor systems. For example, an illustrative aromatization reactor vessel can comprise (i) a reactor wall; (ii) a catalyst bed positioned within the reactor vessel; (iii) an outer annulus positioned between the reactor wall and an outer particle barrier, the outer particle barrier and the outer annulus surrounding the catalyst bed; (iv) a reactor inlet for a feed stream; and (v) a reactor outlet connected to a center pipe, the center pipe positioned in the reactor vessel and surrounded by the catalyst bed. The catalyst bed can comprise an outer reforming zone and an inner reforming zone, the outer reforming zone comprising a deactivated first aromatization catalyst comprising a first transition metal and a first catalyst support, and the inner reforming zone comprising a second aromatization catalyst comprising a second transition metal and a second catalyst support. A flow path for the feed stream can begin at the reactor inlet; continue to the outer annulus; through the outer particle barrier, the outer reforming zone, and the inner reforming zone; into the center pipe; and to the reactor outlet.

In these and other aspects of the invention, the first transition metal and the second transition metal can be the same or different. Likewise, the first catalyst support and the second catalyst support can be the same or different.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE DRAWINGS

The accompanying drawings, which are incorporated in and constitute a part of this disclosure, illustrate various aspects of the present invention. In the drawings.

DEFINITIONS

Figure 1:
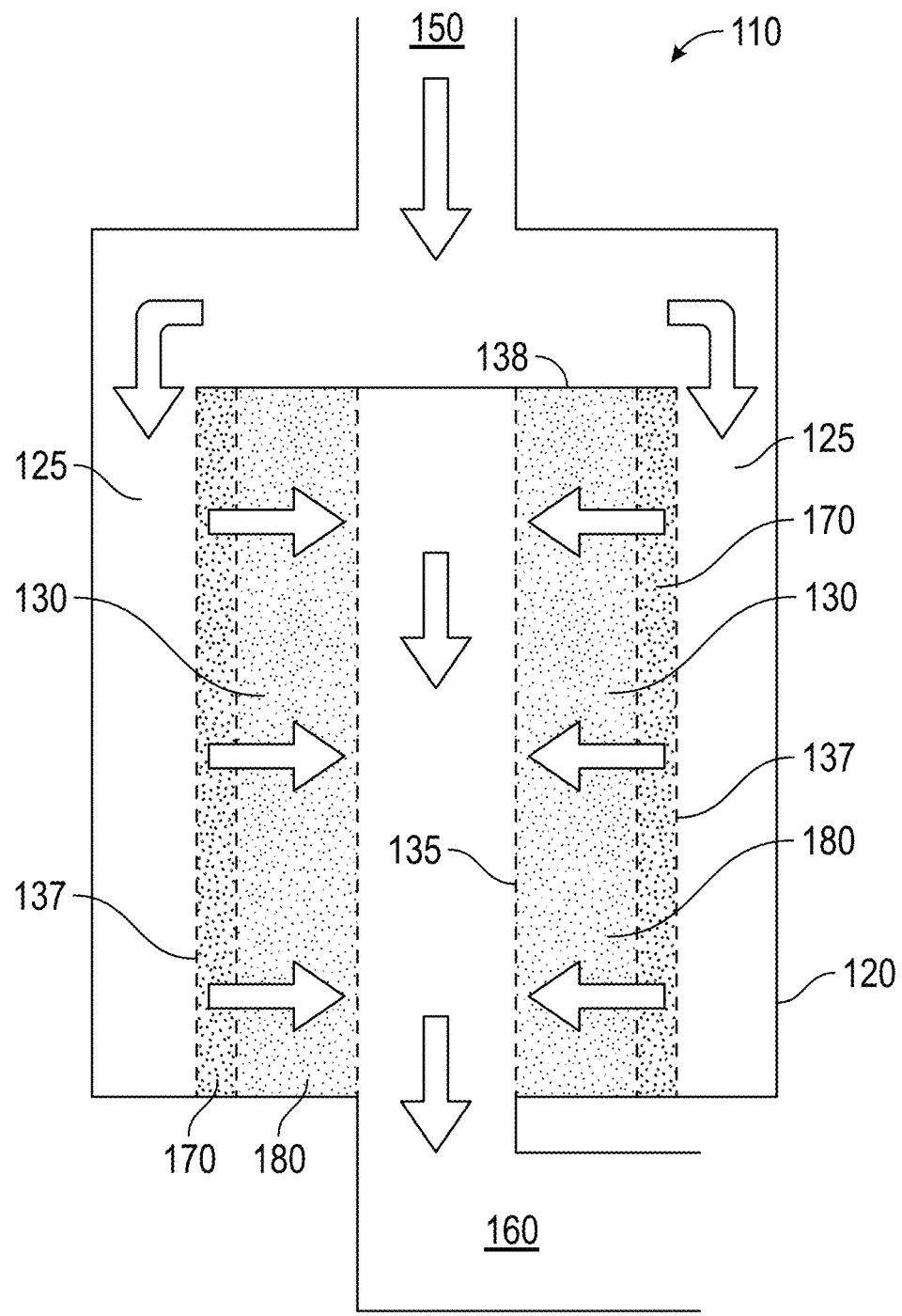
FIG. 1 illustrates a partial cross-sectional view of an aromatization reactor vessel with an outer reforming zone and an inner reforming zone, in an aspect of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein can be combined to describe inventive designs, compositions, processes, or methods consistent with the present disclosure.

While apparatuses, systems, and methods/processes are described herein in terms of "comprising" various components, devices, or steps, the apparatuses, systems, and methods/processes can also "consist essentially of" or "consist of" the various components, devices, or steps, unless stated otherwise.

The terms "a," "an," and "the" are intended to include plural alternatives, e.g., at least one. For instance, the disclosure of "a transition metal" or "a catalyst poisoning agent," is meant to encompass one, or mixtures or combinations of more than one, transition metal or catalyst poisoning agent, unless otherwise specified.

A "spent" catalyst is used herein generally to describe a catalyst that has unacceptable performance in one or more of catalyst activity, hydrocarbon feed conversion, yield to a desired product(s), selectivity to a desired product(s), or an operating parameter, such as maximum operating temperature or pressure drop across a reactor, although the determination that a catalyst is "spent" is not limited only to these features. The unacceptable performance of the spent catalyst can be due to a carbonaceous build-up on the catalyst over time, but is not limited thereto. A "deactivated" or "poisoned" catalyst has substantially no activity to catalyze an aromatization reaction or to catalyze a cracking reaction. A spent catalyst can be contacted with a catalyst poisoning agent, which effectively kills the activity of the resultant deactivated or poisoned catalyst. In some aspects, the "fresh" catalyst can have an activity X, the "spent" catalyst can have an activity Y, and the "deactivated" catalyst or "poisoned" catalyst can have an activity Z, such that $Z<Y<X$. Thus, the activity of the spent catalyst is less than that of the fresh catalyst, but greater than that of the deactivated/poisoned catalyst (which can have no measurable catalyst activity). Catalyst activity comparisons (and other reforming performance characteristics, such as aromatics yield and selectivity) are meant to use the same production run (batch) of catalyst, tested on the same equipment, and under the same test method and conditions.

The amounts of any components or materials present on the catalysts described herein are on a weight basis, such as wt. % or ppmw (ppm by weight), unless otherwise specified. These components or materials can include, for instance, the amount of carbon, the amount of fluorine, the amount of chlorine, the amount of platinum, and so forth.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, noble metals for Group 8-10 elements, and halogens or halides for Group 17 elements.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present application discloses that the methods provided herein can employ a catalyst containing F and Cl at a molar ratio of F:Cl in a range from about 0.5:1 to about 4:1 in certain aspects. By a disclosure that the molar ratio of F:Cl can be in a range from about 0.5:1 to about 4:1, the intent is to recite that the molar ratio can be any molar ratio within the range and, for example, can be equal to about 0.5:1, about 0.6:1, about 0.7:1, about 0.8:1, about 0.9:1, about 1:1, about 2:1, about 3:1, or about 4:1. Additionally, the molar ratio of F:Cl can be within any range from about 0.5:1 to about 4:1 (for example, the molar ratio can be in a range from about 0.5:1 to about 2:1), and this also includes any combination of ranges between about 0.5:1 and about 4:1. Likewise, all other ranges disclosed herein should be interpreted in a manner similar to this example.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The term "substituted" when used to describe a group, for example, when referring to a substituted analog of a particular group, is intended to describe any non-hydrogen moiety that formally replaces a hydrogen atom in that group, and is intended to be non-limiting. A group or groups can also be referred to herein as "unsubstituted" or by equivalent terms such as "non-substituted," which refers to the original group in which a non-hydrogen moiety does not replace a hydrogen atom within that group. Unless otherwise specified, "substituted" is intended to be non-limiting and include inorganic substituents or organic substituents as understood by one of ordinary skill in the art.

As used herein, the term "hydrocarbon" refers to a compound containing only carbon and hydrogen atoms. Other identifiers can be utilized to indicate the presence of particular groups, if any, in the hydrocarbon (e.g., halogenated hydrocarbon indicates that the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (aromatic hydrocarbon compounds, e.g., benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" can be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers can be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group can be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers can be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

The term "contacting" is used herein to describe methods, processes, and compositions wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the methods, processes, and compositions described herein. Combining additional materials or components can be done by any suitable technique. Further, "contacting" two or more components can result in a solution, a slurry, a mixture, a reaction mixture, or a reaction product.

Molar selectivities are defined as:

$$\text{Benzene selectivity:} \quad S_{Bz} = \frac{\dot{n}_{Bz,prod}}{\dot{n}_{conv\ C6,feed} - \dot{n}_{conv\ C6,prod}} \qquad \text{Eq. 1}$$

$$\text{Toluene selectivity:} \quad S_{Tol} = \frac{\dot{n}_{Tol,prod}}{\dot{n}_{conv\ C7,feed} - \dot{n}_{conv\ C7,prod}} \qquad \text{Eq. 2}$$

$$\begin{array}{l}\text{Benzene} + \\ \text{Toluene selectivity:}\end{array} S_{Bz+Tol} = \frac{\dot{n}_{Bz,prod} + \dot{n}_{Tol,prod}}{\dot{n}_{conv\ C6,C7,feed} - \dot{n}_{conv\ C6,C7,prod}} \qquad \text{Eq. 3}$$

$$\text{Aromatics selectivity:} \quad S_{arom} = \frac{\dot{n}_{Bz,prod} + \dot{n}_{Tol,prod} + \dot{n}_{C8+arom,prod}}{\dot{n}_{conv\ C6-C8+,feed} - \dot{n}_{conv\ C6-C8+,prod}} \qquad \text{Eq. 4}$$

Conversion is defined as the number of moles converted per mol of "convertible" hydrocarbons fed:

$$\text{C6 conversion:} \quad X_{C6} = \frac{\dot{n}_{conv\ C6,feed} - \dot{n}_{conv\ C6,prod}}{\dot{n}_{conv\ C6,feed}} \qquad \text{Eq. 5}$$

$$\text{C7 conversion:} \quad X_{C7} = \frac{\dot{n}_{conv\ C7,feed} - \dot{n}_{conv\ C7,prod}}{\dot{n}_{conv\ C7,feed}} \qquad \text{Eq. 6}$$

$$\text{C6} + \text{C7 conversion:} \quad X_{C6+C7} = \frac{\dot{n}_{conv\ C6,feed} + \dot{n}_{conv\ C7,feed} - \dot{n}_{conv\ C6,prod} - \dot{n}_{conv\ C7,prod}}{\dot{n}_{conv\ C6,feed} + \dot{n}_{conv\ C7,feed}} \qquad \text{Eq. 7}$$

In these equations, n indicates a molar flow rate in a continuous reactor or the number of moles in a batch reactor.

As used herein, the term "convertible hydrocarbon," "convertible $C_6$ species," or "convertible $C_7$ species" refers to a hydrocarbon compound that is readily reacted to form aromatic hydrocarbons under aromatization process conditions. A "non-convertible hydrocarbon" is a highly-branched hydrocarbon that is not readily reacted to form aromatic hydrocarbons under aromatization process conditions. A "non-convertible hydrocarbon" can comprise highly-branched hydrocarbons having six or seven carbon atoms with an internal quaternary carbon, or hydrocarbons having six carbons atoms and two adjacent internal tertiary carbons, or mixtures thereof. A "convertible $C_6$ species" is a hydrocarbon containing six carbons without an internal quaternary carbon or two adjacent internal tertiary carbons, for example, n-hexane, 2-methyl-pentane, 3-methyl-pentane, cyclohexane, and methyl cyclopentane. A "convertible $C_7$ species" is a hydrocarbon containing seven carbons without an internal quaternary carbon, for example, n-heptane, 2-methyl-hexane, 3-methyl-hexane, 2,3-dimethyl-pentane, 2,4-dimethyl-pentane, methyl cyclohexane, and dimethyl cyclopentane. The highly branched hydrocarbons with six or seven carbon atoms and an internal quaternary carbon can comprise, for example, 2,2-dimethylbutane, 2,2-dimethyl-pentane, 3,3-dimethylpentane, and 2,2,3-trimethylbutane. The highly branched hydrocarbons with six carbon atoms and an adjacent internal tertiary carbon can comprise, for example, 2,3-dimethylbutane. The non-convertible highly branched hydrocarbons do not easily convert to aromatic products, and instead tend to convert to light hydrocarbons under aromatization process conditions.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The following detailed description refers to the accompanying drawings. Wherever possible, the same or similar reference numbers are used in the drawings and the following description to refer to the same or similar elements or features. While various aspects of the invention are described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description and its exemplary aspects do not limit the scope of the invention.

Beneficially, the aromatization reactor vessels, reactor systems, and reforming methods disclosed herein employ a poisoned or deactivated aromatization catalyst, in place of a spent aromatization catalyst, to unexpectedly result in improved aromatics yield and selectivity. By selectively poisoning the "spent" catalyst residing in the outer reforming zone (closest to the outer annulus), surprisingly, the overall aromatics yield and selectivity within the reactor can be increased.

Aromatization Reactor Vessels and Systems

Generally, aromatization reactor vessels consistent with the present invention can comprise (i) a reactor wall; (ii) a catalyst bed positioned within the reactor vessel; (iii) an outer annulus positioned between the reactor wall and an outer particle barrier, the outer particle barrier and the outer annulus surrounding the catalyst bed; (iv) a reactor inlet for a feed stream; and (v) a reactor outlet connected to a center pipe, the center pipe positioned in the reactor vessel and surrounded by the catalyst bed. The catalyst bed can comprise an outer reforming zone and an inner reforming zone, the outer reforming zone comprising a deactivated first aromatization catalyst comprising a first transition metal and a first catalyst support, and the inner reforming zone comprising a second aromatization catalyst comprising a second transition metal and a second catalyst support. A flow path for the feed stream begins at the reactor inlet; continues to the outer annulus; through the outer particle barrier, the outer reforming zone, and the inner reforming zone; into the center pipe; and to the reactor outlet.

FIG. 1 illustrates an aromatization reactor vessel 110 consistent with the present invention. While not being limited thereto, the aromatization reactor vessel 110 is described herein as it pertains to its use in the catalytic conversion of a non-aromatic hydrocarbon to produce an aromatic hydrocarbon, examples of which include benzene, toluene, or xylenes, as well as mixtures thereof. The aromatization reactor vessel 110 in FIG. 1 can include a reactor wall 120, a center pipe 135 surrounded by a catalyst bed 130, an outer particle barrier 137 surrounding the catalyst bed, and an outer annulus 125 between the outer particle barrier 137 and the reactor wall 120. The reactor vessel 110 can further include a reactor inlet 150 for feed stream, a top cover plate 138, and a reactor outlet 160 through which flows a reactor effluent stream. The reactor outlet 160 is connected to the center pipe 135 as shown in FIG. 1. The catalyst bed 130 comprises an outer reforming zone 170 and an inner reforming zone 180. The arrows in FIG. 1 illustrate a typical flow path for a feed stream entering the aromatization reactor vessel 110, for instance, starting at the reactor inlet 150; then directed to the outer annulus 125 by the top cover plate 138; then through the outer particle barrier 137, and the catalyst bed 130 (first the outer reforming zone 170, then the inner reforming zone 180), into the center pipe 135, and finally to the reactor outlet 160 as reactor effluent.

In FIG. 1, the outer particle barrier 137 in the aromatization reactor vessel 110 can be formed in any number of ways, including employing scallops, outer baskets, and the like. An outer basket more closely resembles what is shown in FIG. 1. An outer basket can have a circular cross-sectional shape. The outer basket has openings that permit the passage of the feed stream, but not the passage of the catalyst particles. The passage of the feed stream can be accomplished by having slots formed into the outer basket, by having a portion of the outer basket formed from a screen or mesh, or combinations thereof. The outer basket can be made from sub-sections that are assembled inside of the reactor vessel.

If desired, the outer annulus 125 can comprise any suitable flow-affecting elements in the flow path to promote flow through the catalyst bed. For example, a "scallop" is a conduit installed adjacent to and vertically along the inside wall of a reactor vessel. The scallops can have a semicircular cross-section or a trapezoidal cross-sectional shape. The scallops have openings that permit the passage of the feed stream, but not the passage of the catalyst particles. The passage of the feed stream can be accomplished by having slots formed into the scallop, by having a portion of the scallop formed from a screen or mesh, or combinations thereof. The scallops fit against the inside of reactor wall 120, with the slots, screen or mesh of the scallops facing the catalyst bed 130. The scallops are typically 8 to 14 inches wide, but are not limited thereto. In an aspect, the screen can comprise welded wires and rods. In a further aspect, the screen can comprise welded Johnson Screens® Vee-Wire® and rods. As a further refinement, slots and screens on the scallop can be oriented vertically to allow catalyst particles to move up and down during processing without becoming abraded by the screen or slot edges. During operation of the aromatization reactor vessel, the scallops can distribute the feed stream along the inside wall or collect the feed stream from the catalyst bed, depending on the direction of flow. In standard flow, the feed flows radially to the center of the reactor vessel across the catalyst bed 130. In the center of the reactor vessel is the process outlet conduit, which can be a vertical perforated pipe, also referred to as a center pipe 135.

The reactor wall 120, the center pipe 135, and other elements of the aromatization reactor vessel 110 in FIG. 1 generally can be cylindrical in shape, but other geometries and orientations can be employed. For instance, as an alternative to a circular cross-section (when viewed from above, such as from the reactor inlet 150), the center pipe can have a rectangular, elliptical, or oval cross-section. Nonetheless, in particular aspects of this invention, the center pipe 135 and the reactor wall 120 are arranged concentrically, or the center pipe 135 and the catalyst bed 130 are arranged concentrically, or the center pipe 135, the catalyst bed 130, and the reactor wall 120 are arranged concentrically, or the center pipe 135, the catalyst bed 130, and the outer particle barrier 137 are arranged concentrically, or the center pipe 135, the catalyst bed 130, the outer particle barrier 137, and the reactor wall 120 are arranged concentrically.

The reactor wall 120, the center pipe 135, the top cover plate 138, the outer particle barrier 137, and other surfaces within the aromatization reactor vessel 110 can be constructed of any suitable metal material, the selection of which can depend upon the desired operating temperature, desired operating pressure, and inertness to the reactor contents (for example, catalyst, $H_2$, aromatic hydrocarbons, non-aromatic hydrocarbons), amongst other factors. Typical metal materials include austenitic stainless steels, including 304, 316, 321, 347, 410S, 600, or 800 stainless steel, and the like. Moreover, a coating or layer containing any suitable material, compound, alloy, or metal, such as tin, can used on any reactor surface (for example, reactor wall 120 or center pipe 135) to provide resistance to carburization and metal dusting; representative protective layer materials are disclosed in U.S. Pat. Nos. 5,866,743, 6,548,030, 8,119,203, and 9,085,736, which are incorporated herein by reference in their entirety. As indicated by the dashed lines in FIG. 1, the center pipe 135 can be porous to allow flow through it, but not so porous that catalyst particles from the catalyst bed 130 can enter the center pipe 135. Hence, the center pipe 135 can comprise screens, mesh sections, perforated metal sheets, or combinations thereof, within the reactor vessel 110. In an aspect, the center pipe 135 can comprise welded wires and rods. In a further aspect, the screen can comprise welded Johnson Screens® VeeWire® and rods. As a further refinement, slots and screens on the center pipe 135 can be oriented vertically to allow catalyst particles to move up and down during processing without becoming abraded by the screen or slot edges.

The aromatization reactor vessel 110 can be configured for operating temperatures that typically fall within the 350° C. to 600° C. range. In one aspect, the reactor vessel 110 can be configured for decreasing temperature from the outer annulus 125 to the center pipe 135, while in another aspect, the reactor vessel 110 can be configured for decreasing temperature from the outer reforming zone 170 to the inner reforming zone 180. In these and other aspects, the reactor vessel 110 can be configured for radial flow, while not being limited thereto. For instance, traditional packed bed reactors can be employed in aspects of this invention.

Likewise, the reactor vessel 110 can be configured for any suitable operating pressure, which can often be at least 20 psig (139 kPag), at least 25 psig (172 kPag), or at least 30 psig (207 kPag), and in some aspects, up to an operating pressure of as much as about 60 psig (414 kPag) to about 100 psig (689 kPag). Hence, typical operating pressures include from about 20 psig (139 kPag) to about 100 psig (689 kPag), or from about 25 psig (172 kPag) to about 60 psig (414 kPag).

While not shown in FIG. 1, the reactor vessel 110 can contain braces, clamps, straps, and the like, as well as combinations thereof, as would be readily recognized by one of ordinary skill in the art, for securing the center pipe 135, the outer particle barrier 137, and other reactor internals.

Additionally, the reactor vessel 110 can further comprise an integrated heat exchange system around at least a portion of the reactor vessel for controlling temperature (heating or cooling) within the reactor vessel, if desired. Additional information on features and designs of aromatization reactor vessels that can be employed in the aromatization reactor vessels described herein is disclosed in U.S. Pat. Nos. 6,548,030, 7,544,335, 7,582,272, 8,119,203, and 9,085,736, which are incorporated herein by reference in their entirety.

Also shown in the aromatization reactor vessel 110 of FIG. 1 is a catalyst bed 130 that contains an outer reforming zone 170 and an inner reforming zone 180. The outer reforming zone is also referred to herein as the first reforming zone, and the inner reforming zone is also referred to herein as the second reforming zone. Consistent with aspects disclosed herein, the outer (or first) reforming zone can comprise a deactivated first aromatization catalyst comprising a first transition metal and a first catalyst support, and the inner (or second) reforming zone can comprise a second aromatization catalyst comprising a second transition metal and a second catalyst support.

The deactivated (or poisoned) first aromatization catalyst in the outer reforming zone generally can be configured to not catalyze an aromatization reaction. For instance, the aromatics yield of the deactivated first aromatization catalyst can be less than 10 wt. %, or less than 5 wt. %, or effectively zero (no catalytic activity), such as under the test methods disclosed in the examples that follow. Additionally or alternatively, the deactivated (or poisoned) first aromatization catalyst in the outer reforming zone generally can be configured to not catalyze a cracking reaction.

The deactivated first aromatization catalyst can result from a spent aromatization catalyst that has been contacted with a catalyst poisoning agent, where the catalyst poisoning agent comprises a material configured to bind to the transition metal such that the transition metal does not catalyze an aromatization reaction and/or does not catalyze a cracking reaction. The mechanism by which the catalyst poisoning agent results in a deactivated aromatization catalyst that does not catalyze an aromatization reaction and/or a cracking reaction is not limited thereto. For instance, the catalyst poisoning agent can comprise a material that causes platinum sintering, platinum agglomeration, and/or pore blockage, as well as any other suitable mechanism, that results in an aromatics yield of the deactivated catalyst of less than 10 wt. %, or less than 5 wt. %, or effectively zero (no catalytic activity); and additionally or alternatively, that results in a deactivated catalyst that does not catalyze a cracking reaction.

In an aspect, the amount of carbon on the deactivated first aromatization catalyst can be in a range from about 1 to about 10 wt. %, from about 1 to about 5 wt. %, from about 1.5 to about 7 wt. % carbon, or from about 1.5 to about 3 wt. %. Additionally, the amount of carbon on the second aromatization catalyst often can be less, such as less than about 0.9 wt. %, or less than about 0.5 wt. %, and representative ranges can include from about 0.01 wt. % to about 0.9 wt. %, from about 0.01 wt. % to about 0.5 wt. %, or from about 0.02 wt. % to about 0.5 wt. %.

While not being limited thereto, the weight ratio (or volume ratio) of the amount of catalyst in the outer reforming zone to the amount of catalyst in the inner reforming zone can be in a range (outer:inner) from about 10:1 to about 1:10, from about 5:1 to about 1:5, or from about 1:3 to about 3:1. In some aspects, the outer reforming zone contains less catalyst than the inner reforming zone, and in these aspects, the outer:inner ratio can be in a range from about 1:1.2 to about 1:10, from about 1:1.5 to about 1:5, or from about 1:2 to about 1:6, and these ratios can be on a weight basis, or on a volume basis. As would be recognized by those of skill in the art, the relative sizes of (or relative amounts of catalyst in) the outer reforming zone and the inner reforming zone can vary as more catalyst in the catalyst bed is deactivated or poisoned.

An unexpected benefit of the reactor vessels disclosed herein can be improved aromatics yield, improved aromatics selectivity, or both. In one aspect, the reactor vessel can be configured for an aromatics yield at the reactor outlet that is greater than that obtained using a spent first aromatization catalyst, instead of the deactivated first aromatization catalyst, in the outer reforming zone. Thus, and surprisingly, replacing a spent catalyst in the outer reforming zone of the catalyst bed (a catalyst with generally poor or unacceptable yield performance) with a deactivated or poisoned catalyst (a catalyst with no aromatics yield) can result in greater overall aromatics yield. In another aspect, the reactor vessel can be configured for an aromatics selectivity at the reactor outlet that is greater than that obtained using a spent first aromatization catalyst, instead of the deactivated first aromatization catalyst, in the outer reforming zone. Thus, and also surprisingly, replacing a spent catalyst in the outer reforming zone of the catalyst bed (a catalyst with generally poor or unacceptable selectivity performance) with a deactivated or poisoned catalyst (a catalyst with no aromatics selectivity) can result in greater overall aromatics selectivity.

The first catalyst support and the second catalyst support, independently, can comprise a zeolite, an amorphous inorganic oxide, or any mixture or combination thereof. For instance, large pore zeolites often can have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often can have average pore diameters in a range of from about 5 Å to about 7 Å. Amorphous inorganic oxides can include, but are not limited to, aluminum oxide, silicon oxide, titania, and combinations thereof. The first catalyst support and the second catalyst support can be the same or different.

The term "zeolite" generally refers to a particular group of hydrated, crystalline aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, hydrogen, or combinations thereof.

In some aspects, the first catalyst support and/or the second catalyst support can comprise an L-type zeolite. L-type zeolite supports are a sub-group of zeolitic supports, which can contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, zinc, or combinations thereof, as well as non-metallic cations like hydronium and ammonium ions, which can be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the first catalyst support and/or the second catalyst support can comprise a potassium L-type zeolite, also referred to as a KL-zeolite, while in another aspect, the first catalyst support and/or the second catalyst support can comprise a barium ion-exchanged L-zeolite. As used herein, the term "KL-zeolite" refers to L-type zeolites in which the principal cation M incorporated in the zeolite is potassium. A KL-zeolite can be cation-exchanged (for example, with barium) or impregnated with a transition metal and one or more halides to produce a transition metal impregnated, halided zeolite or a KL supported transition metal-halide zeolite catalyst.

In the first catalyst support and the second catalyst support, the zeolite can be bound with a support matrix (or binder), non-limiting examples of which can include silica, alumina, magnesia, boria, titania, zirconia, various clays, and the like, including mixed oxides thereof, as well as mixtures thereof. For example, the first catalyst support and/or the second catalyst support can comprise a binder comprising alumina, silica, a mixed oxide thereof, or a mixture thereof. The zeolite can be bound with the binder using any method known in the art. In a particular aspect of this invention, the first catalyst support, the second catalyst support, or both the first catalyst support and the second catalyst support, can comprise a silica-bound KL-zeolite.

While not being limited thereto, the first catalyst support and the second catalyst support, independently, can comprise from about 5 wt. % to about 35 wt. % binder. For example, the first catalyst support and the second catalyst support, independently, can comprise from about 5 wt. % to about 30 wt. %, or from about 10 wt. % to about 30 wt. % binder. These weight percentages are based on the total weight of the (first or second) catalyst support.

The deactivated first aromatization catalyst can comprise a first transition metal and a first catalyst support, and the second aromatization catalyst can comprise a second transition metal and a second catalyst support. The first transition metal and the second transition metal can be the same or different, and can comprise a Group 7-11 transition metal or, alternatively, a Group 8-11 transition metal. In some aspects, the deactivated first aromatization catalyst and/or the second aromatization catalyst can comprise a Group 14 metal such as tin, while in other aspects, the first transition metal and/or the second transition metal can comprise a transition metal, and non-limiting examples of suitable transition metals can include iron, cobalt, nickel, ruthenium, rhodium, palladium, osmium, iridium, rhenium, platinum, gold, silver, copper, and the like, or a combination of two or more transition metals.

For example, the deactivated first aromatization catalyst and/or the second aromatization catalyst can comprise platinum, rhenium, tin, iron, gold, or any combination thereof. Alternatively, the first transition metal and/or the second transition metal can comprise a Group 7-11 transition metal (for example, one or more of platinum, rhenium, and gold), and in another aspect, the first transition metal and/or the second transition metal can comprise a Group 10 transition metal, while in yet another aspect, the first transition metal and the second transition metal can comprise platinum (Pt).

Typically, the deactivated first aromatization catalyst and the second aromatization catalyst can comprise from about 0.1 wt. % to about 10 wt. % transition metal. In another aspect, the deactivated first aromatization catalyst and/or the second aromatization catalyst can comprise from about 0.3 wt. % to about 5 wt. % transition metal. In yet another aspect, the deactivated first aromatization catalyst and/or the second aromatization catalyst can comprise from about 0.3 wt. % to about 3 wt. % transition metal, or from about 0.5 wt. % to about 2 wt. % transition metal. These weight percentages are based on the total weight of the (first or second) aromatization catalyst. In circumstances where the transition metal comprises platinum, the deactivated first aromatization catalyst and/or the second aromatization catalyst can comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum.

In an aspect, the deactivated first aromatization catalyst, the second aromatization catalyst, or both, can comprise platinum on a L-zeolite. In another aspect, the deactivated first aromatization catalyst, the second aromatization catalyst, or both, can comprise platinum on a KL-zeolite. In yet another aspect, the deactivated first aromatization catalyst, the second aromatization catalyst, or both, can comprise platinum on a silica-bound KL-zeolite.

Additionally, the deactivated first aromatization catalyst and the second aromatization catalyst can further comprise a halogen, such as chlorine, fluorine, bromine, iodine, or a combination of two or more halogens. For example, the deactivated first aromatization catalyst and/or the second aromatization catalyst can comprise chlorine, or fluorine, or both chlorine and fluorine.

Chlorine can be present in the deactivated first aromatization catalyst, the second aromatization catalyst, or both, in an amount of from about 0.01 wt. % to about 5 wt. %, from about 0.1 wt. % to about 2 wt. %, or from about 0.3 wt. % to about 1.3 wt. %. Likewise, the deactivated first aromatization catalyst, the second aromatization catalyst, or both, can comprise from about 0.01 wt. % to about 5 wt. % fluorine, from about 0.1 wt. % to about 2 wt. % fluorine, or from about 0.3 wt. % to about 1.3 wt. % fluorine. These weight percentages are based on the total weight of the respective aromatization catalyst. In certain aspects, the deactivated first aromatization catalyst, the second aromatization catalyst, or both, comprise(s) chlorine and fluorine, and typically, the molar ratio of fluorine:chlorine independently can be in the range of from about 0.2:1 to about 4:1. Other suitable molar ratios of F:Cl can include the following non-limiting ranges: from about 0.3:1 to about 4:1, from about 0.5:1 to about 4:1, from about 0.2:1 to about 2:1, from about 0.3:1 to about 2:1, or from about 0.5:1 to about 2.5:1.

Examples of representative and non-limiting catalysts that can be used as the first aromatization catalyst (prior to deactivation or poisoning) and/or the second aromatization catalyst include those disclosed in U.S. Pat. Nos. 5,196,631, 6,190,539, 6,406,614, 6,518,470, 6,812,180, 7,153,801, and 7,932,425, the disclosures of which are incorporated herein by reference in their entirety.

Also encompassed herein are aromatization reactor vessel systems, and such systems generally can comprise two or more aromatization reactor vessels in series, at least one of which is any of the aromatization reactor vessels described hereinabove (i.e., with the catalyst bed 130 containing the outer reforming zone 170 and the inner reforming zone 180). For example, an exemplary reactor system can comprise any suitable number of reactor vessels in series, such as from 2 to 8 vessels, from 2 to 7 vessels, from 3 to 8 vessels, from 4 to 7 vessels, 5 vessels, 6 vessels, 7 vessels, or 8 vessels, in series. The reactor system can either be configured for a single pass of the non-aromatic hydrocarbon through the series of reactor vessels, or the reactor system can be configured to separate the unreacted non-aromatic hydrocarbons from the aromatic hydrocarbons, with subsequent recycling of the unreacted non-aromatic hydrocarbons to the first reactor vessel in the series.

In the series of reactor vessels, the specific vessel (or vessels) with the catalyst bed 130 containing the outer reforming zone 170 and the inner reforming zone 180 is not particularly limited. For instance, the reactor vessel with the catalyst bed 130 containing the outer reforming zone 170 and the inner reforming zone 180 can be the first, second, third, fourth, or fifth vessel in the series, or the third or fourth vessel in the series. Additionally, more than one reactor vessel with a catalyst bed containing an outer reforming zone and an inner reforming zone can be present.

The aromatization reactor vessel system can further comprise a furnace before any or each reactor vessel in the series, and the furnace can be capable of heating any feed stream to a reactor vessel operating temperature of from about 350° C. to about 600° C. Typically, the reactor vessel system contains a furnace before the first reactor vessel in the series. Also typically, the reactor vessel system contains a furnace before each reactor vessel in the series. Each furnace can be configured to heat a reactor effluent of the previous reactor vessel in the series to a temperature of from about 350° C. to about 600° C. before entering the next vessel in the series. A transfer pipe can be positioned between and connect each furnace and respective upstream and downstream reactor vessel.

Figure 2:
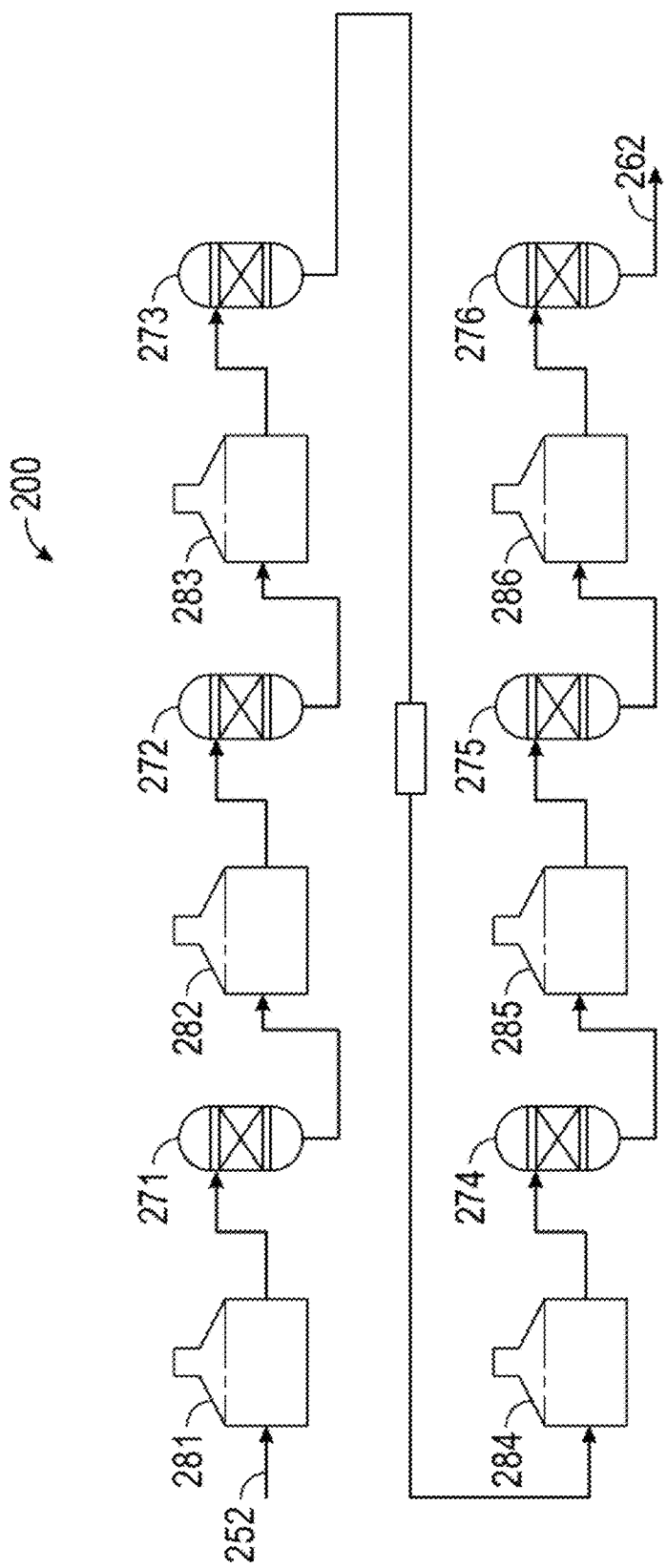
FIG. 2 illustrates a reactor system containing a series of furnaces and reactor vessels, in another aspect of the present invention.

FIG. 2 presents an illustrative example of an aromatization reactor vessel system 200 comprising an aromatization reactor vessel with a catalyst bed 130 containing the outer reforming zone 170 and the inner reforming zone 180. In FIG. 2, six reactor vessels 271, 272, 273, 274, 275, 276 are shown in series, with a corresponding furnace 281, 282, 283, 284, 285, 286 preceding each respective reactor vessel in the system 200. The furnaces 281, 282, 283, 284, 285, 286 in FIG. 2 can be capable of heating or reheating any feed stream or reactor effluent to a reactor vessel operating temperature of from about 350° C. to about 600° C. A feed stream 252 enters the first furnace 281 and then the first reactor vessel 271. Each reactor vessel can be configured to contact the feed stream with an aromatization catalyst to catalytically convert at least a portion of the non-aromatic hydrocarbon to produce an aromatic hydrocarbon (for example, benzene, toluene, xylenes, and the like, as well as combinations thereof). Progressively more of the non-aromatic hydrocarbon is converted to the aromatic hydrocarbon, starting with the more easily converted non-aromatic hydrocarbons, as each reactor vessel in the series has been traversed. A final reactor effluent 262 exits the last reactor vessel 276 in the system 200.

The aromatization reactor vessel with the catalyst bed 130 containing the outer reforming zone 170 and the inner reforming zone 180 can be placed at any suitable location in the system 200 and series of reactor vessels, and more than one such reactor vessel can be used. The aromatization reactor vessel system 200 shown in FIG. 2 contains six reactor vessels in series, although any suitable number of reactor vessels in series can be used, such as, for example, from 2 to 8 reactor vessels, from 2 to 7 reactor vessels, from 3 to 8 reactor vessels, from 4 to 7 reactor vessels, 5 reactor vessels, 6 reactor vessels, 7 reactor vessels, or 8 rector vessels. The reactor system can either be configured for a single pass of the non-aromatic hydrocarbon through the series of reactor vessels, or the reactor system can be configured to separate the unreacted non-aromatic hydrocarbons from the aromatic hydrocarbons, with subsequent recycling of the unreacted non-aromatic hydrocarbons to the first reactor vessel in the series.

Reforming Methods

Aspects of this invention also are directed to aromatization or reforming methods. A first reforming method provided herein can comprise (or consist essentially of, or consist of) (a) providing a radial flow reactor comprising a catalyst bed, the catalyst bed comprising an outer (or first) reforming zone and an inner (or second) reforming zone; wherein the outer reforming zone can comprise a spent first aromatization catalyst comprising a first transition metal and a first catalyst support; and the inner reforming zone can comprise a second aromatization catalyst comprising a second transition metal and a second catalyst support; (b) introducing a catalyst poisoning agent (or catalyst deactivating agent) into the radial flow reactor and contacting at least a portion of the spent first aromatization catalyst in the outer reforming zone (to partially or completely deactivate the portion of the spent first aromatization catalyst); and (c) introducing a hydrocarbon feed into the radial flow reactor comprising the catalyst bed, and contacting the hydrocarbon feed with the catalyst bed under reforming conditions to produce an aromatic product.

A second reforming method provided herein can comprise (or consist essentially of, or consist of) (A) introducing a first hydrocarbon feed into a radial flow reactor comprising a catalyst bed, and contacting the first hydrocarbon feed with the catalyst bed under first reforming conditions to produce a first aromatic product; wherein the catalyst bed can comprise an outer (or first) reforming zone and an inner (or second) reforming zone; the outer reforming zone can comprise a first aromatization catalyst comprising a first transition metal and a first catalyst support; and the inner reforming zone can comprise a second aromatization catalyst comprising a second transition metal and second catalyst support; (B) performing step (A) for a time period sufficient to form a spent first aromatization catalyst in the outer reforming zone; (C) introducing a catalyst poisoning agent (or catalyst deactivating agent) into the radial flow reactor and contacting at least a portion of the spent first aromatization catalyst in the outer reforming zone (to partially or completely deactivate the portion of the spent first aromatization catalyst); and (D) introducing a second hydrocarbon feed into the radial flow reactor comprising the catalyst bed, and contacting the second hydrocarbon feed with the catalyst bed under second reforming conditions to produce a second aromatic product. Step (B) in this second reforming method indicates that step (A) can be performed for a time period sufficient for the first aromatization catalyst to become "spent." As discussed herein above, a "spent" catalyst is typically a catalyst that has unacceptable performance in one or more of catalyst activity, hydrocarbon feed conversion, yield to a desired product(s), selectivity to a desired product(s), or an operating parameter, such as maximum operating temperature or pressure drop across a reactor, although not limited thereto. Once the first aromatization catalyst is "spent," the catalyst deactivation/poisoning step (C), amongst others, can be performed.

Generally, the features of the first and second methods (for example, the first and second hydrocarbon feed, the first and second aromatization catalyst, the first and second aromatic product, and inner and outer reforming zones, among others) are independently described herein and these features can be combined in any combination to further describe the disclosed reforming methods. Moreover, other process steps can be conducted before, during, and/or after any of the steps listed in this first and second methods, unless stated otherwise.

In these methods, the hydrocarbon feed, the first hydrocarbon feed, and the second hydrocarbon feed, independently, can comprise non-aromatic hydrocarbons, such as $C_6$-$C_9$ alkanes and/or cycloalkanes, or $C_6$-$C_8$ alkanes and/or cycloalkanes. Further, the hydrocarbon feed, the first hydrocarbon feed, and the second hydrocarbon feed, independently, can comprise hexane, heptane, or a combination thereof. It is contemplated that the first hydrocarbon feed and the second hydrocarbon feed can be the same or different. Typically, the aromatic product, the first aromatic product, and the second aromatic product, formed in these reforming methods independently can comprise benzene, toluene, or a combination thereof. Suitable reforming conditions, first reforming conditions, and second reforming conditions, independently, can encompass the same ranges disclosed hereinabove in relation to the reactor vessel operating conditions. For example, the reforming conditions, the first reforming conditions, and the second reforming conditions, independently, can comprise a reforming temperature in a range from about 350° C. to about 600° C. (or from about 400° C. to about 600° C.) and a reforming pressure in a range from about 20 psig (138 kPag) to about 100 psig (689 kPag) (or from about 25 to about 60 psig (about 172 to about 414 kPag)). Further, the temperature of the hydrocarbon feed, the first hydrocarbon feed, and the second hydrocarbon feed can decrease from the outer reforming zone to the inner reforming zone. Other suitable non-aromatic hydrocarbon feed materials, aromatic hydrocarbon products, and aromatization or reforming conditions for use in the disclosed methods for catalytically converting non-aromatic hydrocarbons to aromatic hydrocarbons are well known to those of skill in the art and are described, for example, in U.S. Pat. Nos. 4,456,527, 5,389,235, 5,401,386, 5,401,365, 6,207,042, 7,932,425, and 9,085,736, the disclosures of which are incorporated herein by reference in their entirety.

In these methods, the first catalyst support and the second catalyst support can be the same or different and, independently, can be any of the catalyst supports disclosed herein as being suitable catalyst support materials for use in an aromatization reactor vessel. For example, the first catalyst support and/or the second catalyst support can comprise a silica-bound KL-zeolite. Likewise, the first transition metal and the second transition metal, independently, can be any of the transition metals disclosed herein as being suitable transition metals for use in an aromatization reactor vessel. For example, the first transition metal and the second transition metal can comprise platinum. Accordingly, the first aromatization catalyst, the second aromatization catalyst, and the spent first aromatization catalyst, independently, can comprise any suitable weight percentage of transition metal (or platinum) or an amount of transition metal (or platinum) in any range disclosed herein, for example, from about 0.1 wt. % to about 10 wt. %, from about 0.3 wt. % to about 5 wt. %, or from about 0.5 wt. % to about 2 wt. %, based on the total weight of the respective aromatization catalyst.

In one aspect, the first aromatization catalyst, the second aromatization catalyst, and the spent first aromatization catalyst, can comprise platinum on a L-zeolite, while in another aspect, the first aromatization catalyst, the second aromatization catalyst, and the spent first aromatization catalyst can comprise platinum on a KL-zeolite, and in yet another aspect, the first aromatization catalyst, the second aromatization catalyst, and the spent first aromatization catalyst can comprise platinum on a silica-bound KL-zeolite.

The first aromatization catalyst, the second aromatization catalyst, and the spent first aromatization catalyst can further comprise a halogen, such as chlorine and/or fluorine. Suitable amounts are disclosed herein, and often range from about 0.01 wt. % to about 5 wt. %, or from about 0.3 to about 1.3 wt. %, of fluorine and chlorine individually. The relative amount of fluorine and chlorine on the respective catalyst also is disclosed herein, and generally falls within a molar ratio range of fluorine:chlorine (F:Cl) from about 0.2:1 to about 4:1.

In an aspect, the amount of carbon on the spent first aromatization catalyst can be in a range from about 1 to about 10 wt. %, from about 1 to about 5 wt. %, from about 1.5 to about 7 wt. % carbon, or from about 1.5 to about 3 wt. %. Additionally, the amount of carbon on the first and second aromatization catalyst often can be less, such as less than about 0.9 wt. %, or less than about 0.5 wt. %, and representative ranges for the amount of carbon on the first aromatization catalyst and second aromatization catalyst, independently, can include from about 0.01 wt. % to about 0.9 wt. %, from about 0.01 wt. % to about 0.5 wt. %, or from about 0.02 wt. % to about 0.5 wt. %.

Generally, the activity (e.g., aromatics yield) of the second aromatization catalyst is greater than that of the spent first aromatization catalyst, and additionally or alternatively, the aromatics selectivity of the second aromatization catalyst is greater than that of the spent first aromatization catalyst. Such comparisons are meant to be performed under the same test conditions.

In step (b) of the first reforming method (and step (C) of the second reforming method), a catalyst poisoning agent (or catalyst deactivating agent) can be introduced into the radial flow reactor and contacted with at least a portion of the spent first aromatization catalyst in the outer reforming zone, thereby partially or completely deactivating any suitable portion or percentage of the spent first aromatization catalyst in the outer reforming zone. The catalyst poisoning agent can be added to the reactor in any conventional manner, such as via the reactor inlet or through a separate feed port, if desired. In an aspect, the catalyst poisoning agent can be fed into the reactor along with the hydrocarbon feed. Additionally or alternatively, the hydrocarbon feed (e.g., a first hydrocarbon feed) can be momentarily halted or discontinued, and the catalyst poisoning agent can then be fed into the reactor, and then the hydrocarbon feed (e.g., a second hydrocarbon feed) to the reactor can be resumed.

The catalyst poisoning (or deactivating) agent can be added to the reactor at any suitable amount. Generally, however, the catalyst poisoning agent can be introduced into the reactor at a molar ratio (moles of the catalyst poisoning agent to moles of transition metal in the spent first aromatization catalyst) in a range from about 0.01:1 to about 1:1, from about 0.01:1 to about 0.5:1, from about 0.05:1 to about 1:1, from about 0.05:1 to about 0.5:1, from about 0.1:1 to about 0.75:1, from about 0.2:1 to about 1:1, from about 0.2:1 to about 0.8:1, from about 0.3:1 to about 0.8:1, from about 0.4:1 to about 1:1, or from about 0.5:1 to about 0.9:1. Thus, any amount—from very little to effectively all—of the spent first aromatization catalyst in the outer reforming zone can be contacted with the catalyst poisoning agent. After contact of the spent first aromatization catalyst with the catalyst poisoning agent, the aromatics yield of the (poisoned or deactivated) spent first aromatization catalyst can be less than 10 wt. %, or less than 5 wt. %, or effectively zero (no catalytic activity), such as under the test methods disclosed in the examples that follow.

The catalyst poisoning agent can comprise any material that is configured to bind to the transition metal (for example, platinum) such that the transition metal does not catalyze an aromatization reaction and/or the transition metal does not catalyze a cracking reaction. As disclosed herein, the mechanism by which the catalyst poisoning agent operates is not limited thereto. The catalyst poisoning agent can comprise a material that causes platinum sintering, platinum agglomeration, and/or pore blockage, as well as any other suitable mechanism, that results in an aromatics yield of the deactivated catalyst of less than 10 wt. %, or less than 5 wt. %, or effectively zero (no catalytic activity); and additionally or alternatively, that results in a deactivated catalyst that does not catalyze a cracking reaction.

While not a requirement, but for ease of use in an operating radial flow reactor, the catalyst poisoning agent can comprise a material that is a gas throughout (or below) any range of temperatures disclosed herein (e.g., reforming temperatures); for example, a gas throughout the temperature range of 200° C. to 800° C., or a gas throughout the temperature range of 300° C. to 700° C.

Illustrative and non-limiting examples of catalyst poisoning agents can include heavy hydrocarbons (e.g., anthracene), sulfur-containing compounds (e.g., $H_2S$; a thiophene such as thiophene, benzothiophene, or dibenzothiophene; a mercaptan), phosphorus-containing compounds (e.g., a phosphate, a phosphine), oxygen-containing compounds (e.g., acetaldehyde), bromine-containing compounds (e.g., a brominated hydrocarbon such as dibromohexane), iodine-containing compounds (e.g., an iodinated hydrocarbon such as iodohexane), organometallic lead compounds (e.g., tetraethyl lead), organometallic arsenic compounds (e.g., trimethylarsine), and the like, as well as combinations of two or more of these poisoning agents. Other suitable catalyst poisoning agents are readily apparent to a skilled artisan in view of this disclosure, and are encompassed herein.

Figure 3:
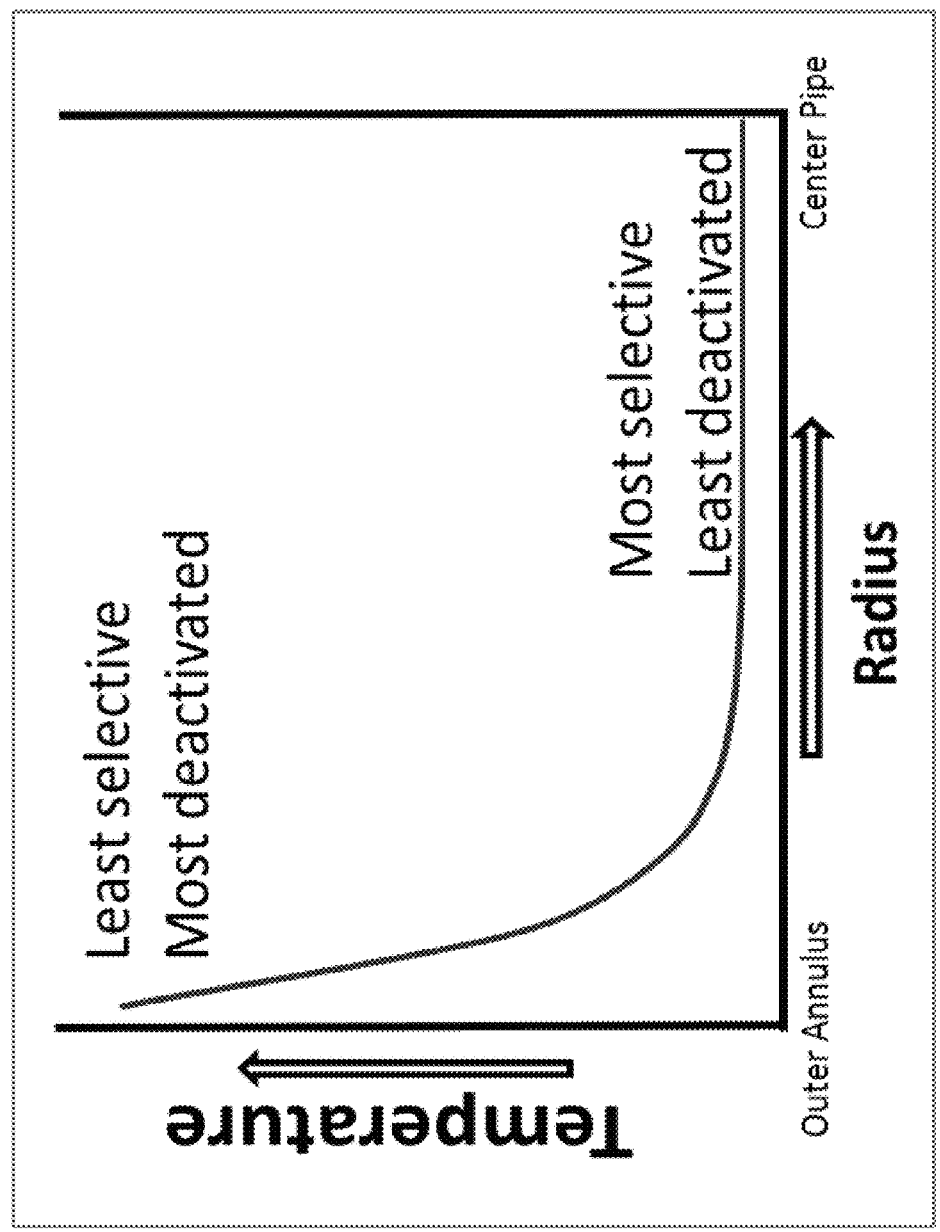
FIG. 3 is a representative plot of the reactor temperature as a function of the location in the reactor, from outer annulus to center pipe, when the catalyst closest to the outer annulus is spent catalyst.
Figure 4:
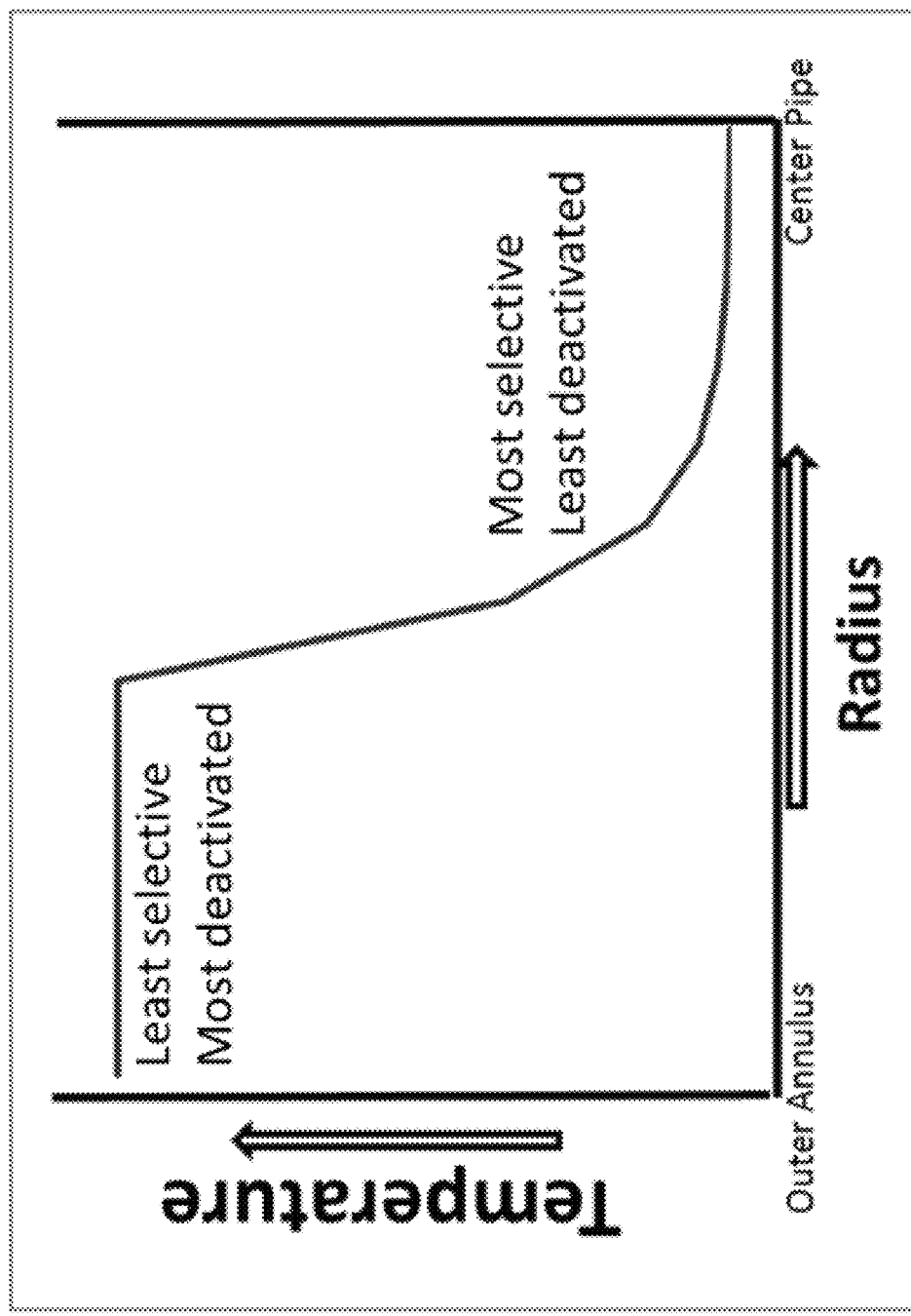
FIG. 4 is a representative plot of the reactor temperature as a function of the location in the reactor, from outer annulus to center pipe, when the catalyst closest to the outer annulus has been deactivated with a catalyst poisoning agent.

Referring now to FIG. 3, which illustrates a representative plot of the reactor temperature as a function of the location in the reactor, from outer annulus to center pipe, when the catalyst closest to the outer annulus is spent. This representation is prior to the introduction of the catalyst poisoning agent. FIG. 4 illustrates a representative plot of the reactor temperature as a function of the location in the reactor, from outer annulus to center pipe, when the catalyst closest to the outer annulus has been deactivated with a catalyst poisoning agent. By poisoning (or completely deactivating) the spent catalyst in the outer reforming zone (closest to the outer annulus), more of the aromatization reaction takes place further in the catalyst bed (inner reforming zone, closer to the center pipe), where the least deactivated or least spent catalyst resides.

Accordingly, one beneficial and unexpected result of the reforming methods disclosed herein—which utilize a catalyst poisoning agent—is improved yield. For instance, the yield of the aromatic product in step (c)—after the addition of the catalyst poisoning agent—can be greater than the yield of an aromatic product produced after step (a) and before step (b). Likewise, the yield of the second aromatic product in step (D)—after the addition of the catalyst poisoning agent—can be greater than the yield of a first aromatic product produced after step (B) and before step (C).

Another beneficial and unexpected result of the reforming methods disclosed herein—which utilize a catalyst poisoning agent—is improved selectivity. For instance, the selectivity of the aromatic product in step (c)—after the addition of the catalyst poisoning agent—can be greater than the aromatics selectivity of an aromatic product produced after step (a) and before step (b). Likewise, the selectivity of the second aromatic product in step (D)—after the addition of the catalyst poisoning agent—can be greater than the aromatics selectivity of the first aromatic product produced after step (B) and before step (C).

While not being limited thereto, the weight ratio (or volume ratio) of the amount of catalyst in the outer reforming zone to the amount of catalyst in the inner reforming zone can be in a range (outer:inner) from about 10:1 to about 1:10, from about 5:1 to about 1:5, or from about 1:3 to about 3:1. In some aspects, the outer reforming zone contains less catalyst than the inner reforming zone, and in these aspects, the outer:inner ratio can be in a range from about 1:1.2 to about 1:10, from about 1:1.5 to about 1:5, or from about 1:2 to about 1:6, and these ratios can be on a weight basis, or on a volume basis. As would be recognized by those of skill in the art, the relative sizes of (or relative amounts of catalyst in) the outer reforming zone and the inner reforming zone can vary as more catalyst in the catalyst bed is deactivated or poisoned by addition of the catalyst poisoning agent.

If desired, the methods disclosed herein can further comprise an inert gas purging step after the catalyst poisoning step, the inert gas purging step comprising introducing an inert gas stream into the radial flow reactor and contacting the catalyst bed. The inert gas stream can comprise (or consist essentially of, or consist of) any suitable inert gas, such as nitrogen or argon. Mixtures of more than one inert gas can be used.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Examples 1-2

In Examples 1-2, the fresh aromatization catalyst was a Pt/KL-zeolite containing approximately 1 wt. % platinum, 0.85 wt. % Cl, and 0.75 wt. % F (determined via XRF), with a surface area of approximately 180 m$^2$/g, a pore volume of 0.2 cc/g, and a micropore volume of 0.06 cc/g. The source of the spent catalyst was the fresh catalyst, but after it had been partially deactivated after long-term use in an aromatization reactor. For Example 1, a sample of the spent catalyst was taken from the section of the catalyst bed closest to the outer annulus of the reactor (near the outer particle barrier). For Example 2, a sample of the spent catalyst was taken from the section of the catalyst bed closest to the center pipe. Prior to usage in these examples, the respective spent catalysts were subjected to a mild partial decoking step to remove unreacted hydrocarbons and light carbonaceous deposits from the catalysts.

The respective spent catalysts were ground and sieved to 25-45 mesh, and 1 cc of each sieved catalyst was placed in a ⅜-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a pressure of 100 psig (689 kPag), a H$_2$:hydrocarbon molar ratio of 1.3:1, and a liquid hourly space velocity (LHSV) of 12 hr$^{-1}$ to obtain catalyst performance data over time. The first 5-6 hours were conducted at 950° F. (510° C.), and the remainder of the 40-hour test was conducted at 980° F. (527° C.). The aliphatic hydrocarbon feed contained approximately 0.64 mole fraction of convertible C$_6$ species and 0.21 mole fraction of convertible C$_7$ species. The balance was attributed to aromatics, C$_8^+$, and highly branched isomers, which are classified as non-convertibles. The reactor effluent composition was analyzed by gas chromatography to determine the total aromatics and the aromatics selectivity.

Figure 5:
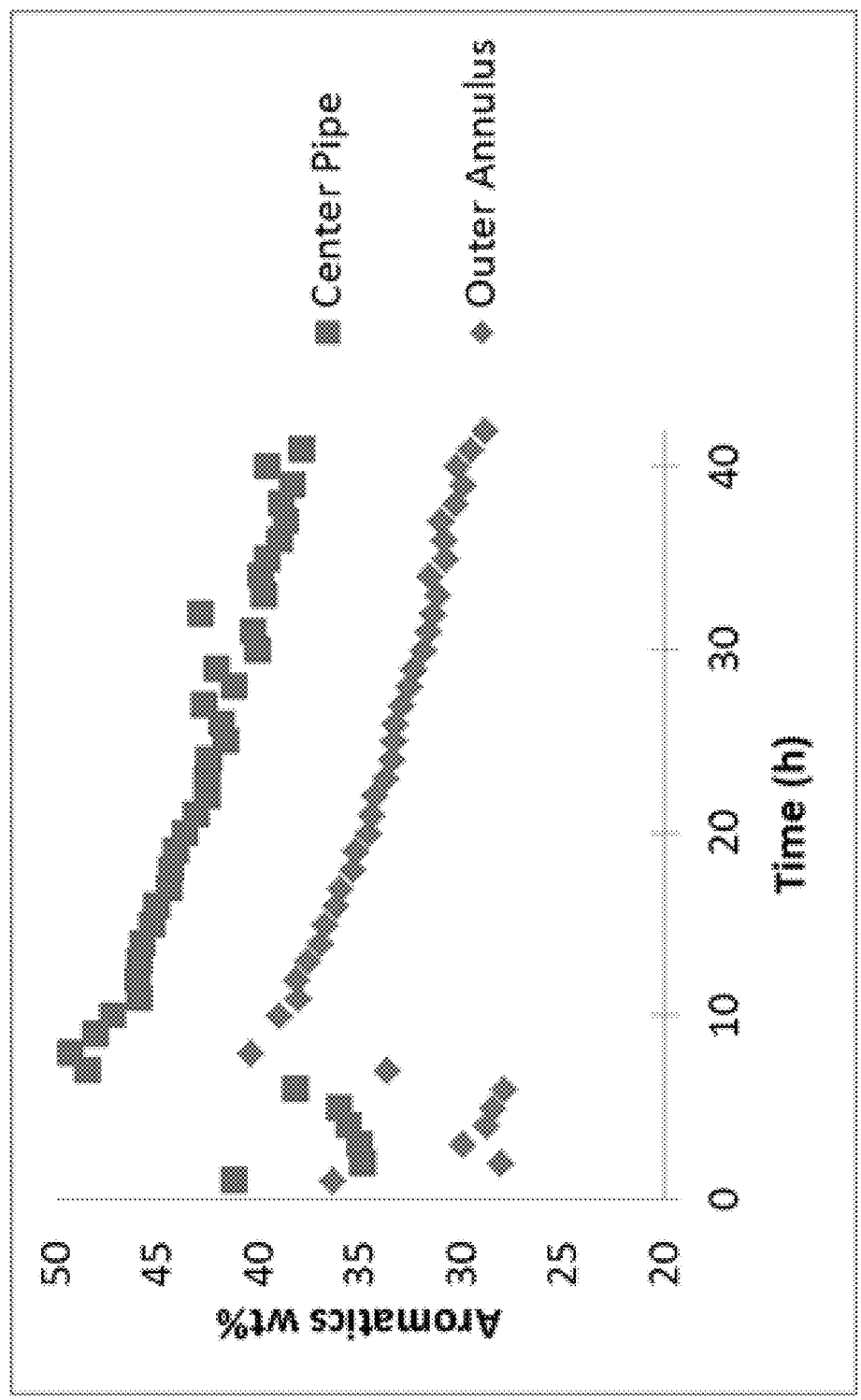
FIG. 5 presents a plot of the aromatics yield versus reaction time for the spent catalyst of Example 1 (closest to the outer annulus) and the spent catalyst of Example 2 (closest to the center pipe).
Figure 6:
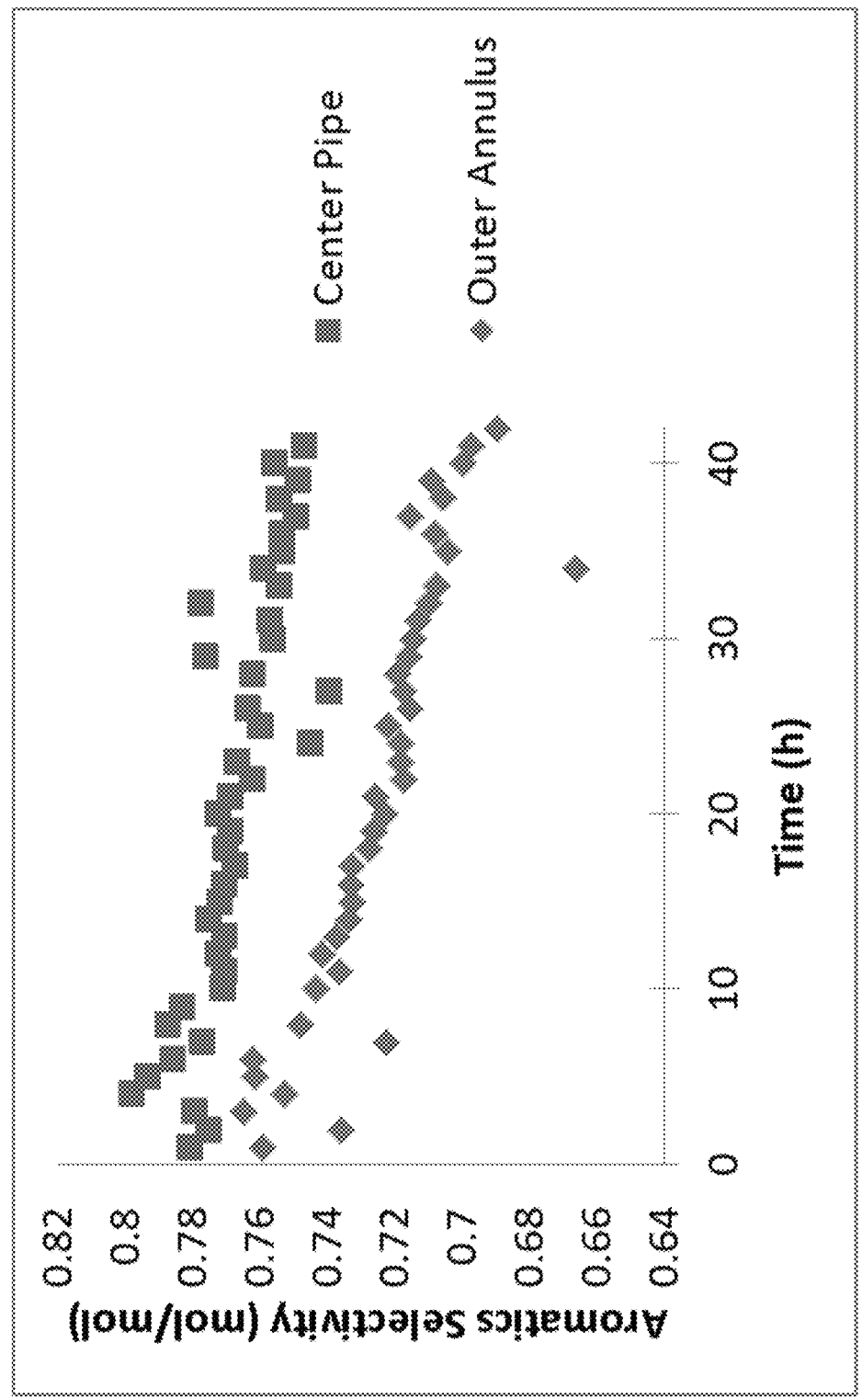
FIG. 6 presents a plot of the aromatics selectivity versus reaction time for the spent catalyst of Example 1 (closest to the outer annulus) and the spent catalyst of Example 2 (closest to the center pipe).

Catalyst activity (aromatics yield) and catalyst selectivity data for the spent catalysts of Examples 1-2 are summarized in FIG. 5 and FIG. 6, respectively. As demonstrated by the lower aromatics yield in FIG. 5, the spent catalyst of Example 1 (closest to the outer annulus) was significantly less active than the spent catalyst of Example 2 (closest to the center pipe). Likewise, FIG. 6 demonstrates that the spent catalyst of Example 1 (closest to the outer annulus) was significantly less selective to aromatics than the spent catalyst of Example 2 (closest to the center pipe).

Examples 1-2, therefore, demonstrate that the catalyst closest to the outer annulus becomes more "spent" and less active and selective (lower aromatics yield, more cracking reactions, lower aromatics selectivity), as compared to the catalyst closest to the center pipe, which has superior catalyst activity and selectivity.

Examples 3-4

In Examples 3-4, the fresh aromatization catalyst was a Pt/KL-zeolite containing approximately 1 wt. % platinum, 0.85 wt. % Cl, and 0.75 wt. % F (determined via XRF), with a surface area of approximately 180 m$^2$/g, a pore volume of 0.2 cc/g, and a micropore volume of 0.06 cc/g. The source of the spent catalyst was the fresh catalyst, but after it had been partially deactivated after long-term use in an aromatization reactor. Examples 3-4 were conducted in generally the same manner as that of Examples 1-2, but with the following differences. Example 3 used a sequential fixed bed with a first zone containing 1 cc of the spent catalyst and a second zone containing 1 cc of fresh catalyst (the hydrocarbon feed contacted the first zone—i.e., the spent catalyst—before the second zone). Example 3 is a reference example, and is illustrative of a reactor with the catalyst closest to the outer annulus being less active and selective (e.g., a spent catalyst), and the catalyst closest to the center pipe having superior activity and selectivity (e.g., fresh catalyst, or spent catalyst that is less deactivated than the catalyst near the outer annulus). Example 4 used a sequential fixed bed with a first zone containing 1 cc of a deactivated (or poisoned)

catalyst and a second zone containing 1 cc of fresh catalyst. The deactivated (or poisoned) catalyst was prepared by immersing a sample of the spent catalyst in a solution of $K_3PO_4$, thereby completely deactivating the catalyst. Catalyst bed performance data over time was conducted at 950° F. (510° C.) for the 40-hour test.

Figure 7:
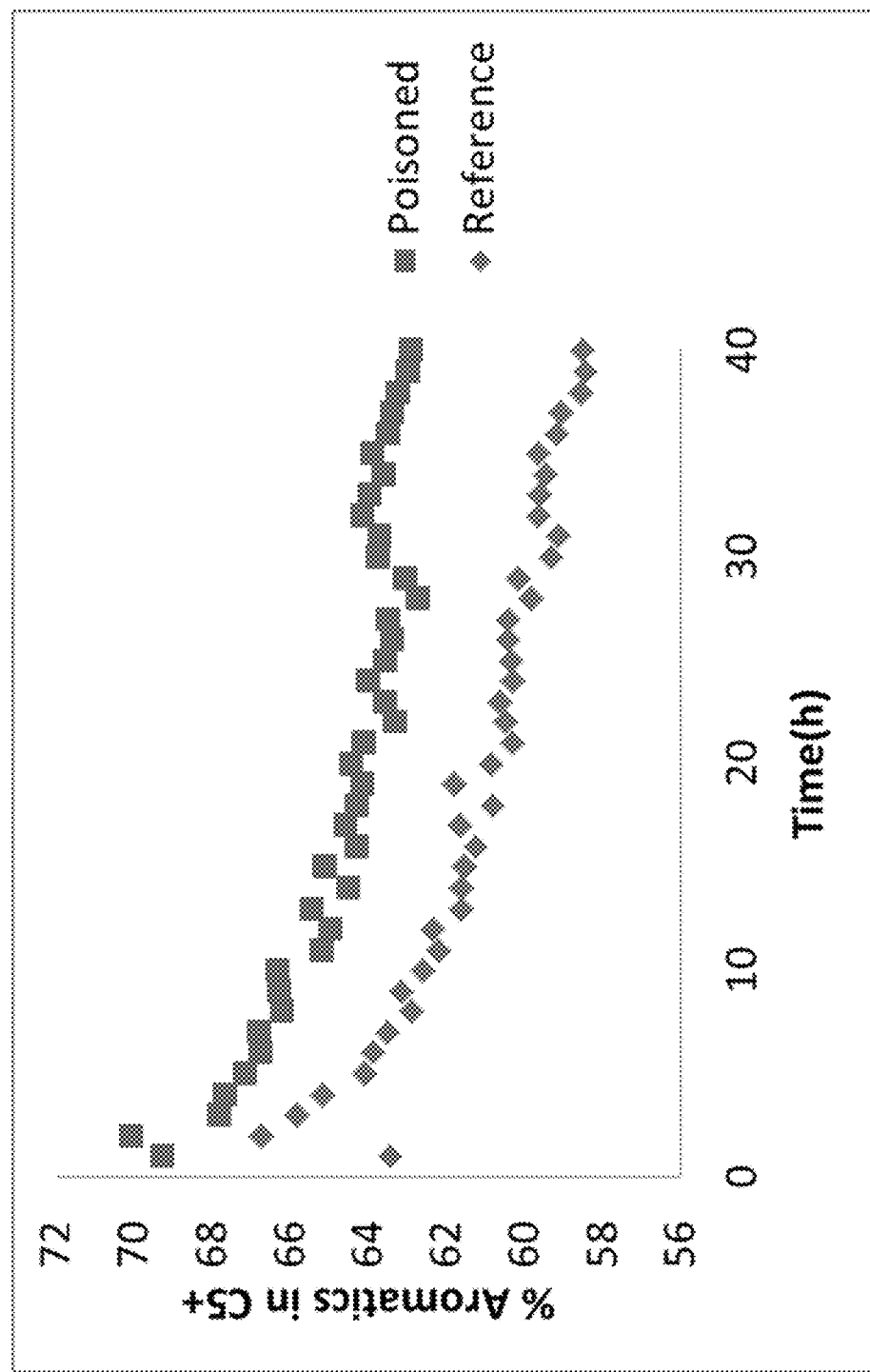
FIG. 7 presents a plot of the aromatics yield versus reaction time for the catalyst bed of Example 3 (reference) and the catalyst bed of Example 4 (with a deactivated or poisoned catalyst zone).
Figure 8:
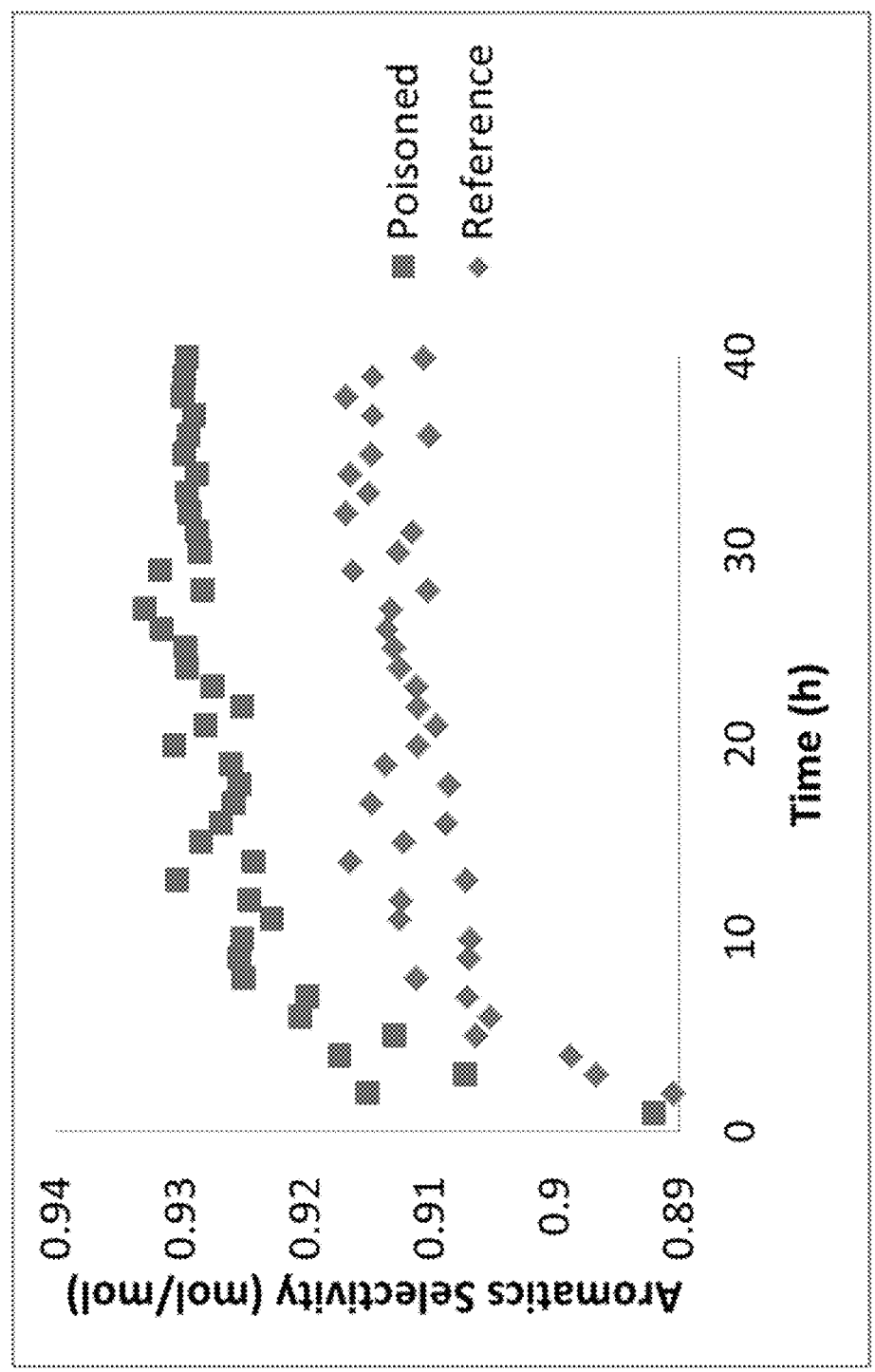
FIG. 8 presents a plot of the aromatics selectivity versus reaction time for the catalyst bed of Example 3 (reference) and the catalyst bed of Example 4 (with a deactivated or poisoned catalyst zone).

Catalyst activity (aromatics yield in $C_5+$) and catalyst selectivity data for the catalyst beds of Examples 3-4 are summarized in FIG. 7 and FIG. 8, respectively. As demonstrated by the higher aromatics yield in FIG. 7, and unexpectedly, the catalyst bed of Example 4 (poisoned:fresh) was significantly more active than the catalyst bed of Example 3 (spent:fresh). Likewise, and also surprisingly, FIG. 8 demonstrates that the catalyst bed of Example 4 was significantly more selective to aromatics than the catalyst bed of Example 3.

Examples 3-4, therefore, demonstrate the unexpected result that an aromatization reactor with spent catalyst closest to the outer annulus results in lower aromatics yield, more cracking reactions, and lower aromatics selectivity, as compared to an aromatization reactor where the catalyst closest to the outer annulus has been completely deactivated (or poisoned). Thus, overall reactor performance—in terms of aromatics yield and aromatics selectivity—can be improved by selectively deactivating/poisoning the spent catalyst closest to the outer annulus.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A reforming method comprising:

(a) providing a radial flow reactor comprising a catalyst bed, the catalyst bed comprising an outer (first) reforming zone and an inner (second) reforming zone; wherein:

the outer reforming zone comprises a spent first aromatization catalyst comprising a first transition metal and a first catalyst support; and the inner reforming zone comprises a second aromatization catalyst comprising a second transition metal and a second catalyst support;

(b) introducing a catalyst poisoning agent (or catalyst deactivating agent) into the radial flow reactor and contacting at least a portion of the spent first aromatization catalyst in the outer reforming zone (to partially or completely deactivate the portion of the spent first aromatization catalyst); and (c) introducing a hydrocarbon feed into the radial flow reactor comprising the catalyst bed, and contacting the hydrocarbon feed with the catalyst bed under reforming conditions to produce an aromatic product.

Aspect 2. A reforming method comprising:

(A) introducing a first hydrocarbon feed into a radial flow reactor comprising a catalyst bed, and contacting the first hydrocarbon feed with the catalyst bed under first reforming conditions to produce a first aromatic product; wherein:

the catalyst bed comprises an outer (first) reforming zone and an inner (second) reforming zone;

the outer reforming zone comprises a first aromatization catalyst comprising a first transition metal and a first catalyst support; and the inner reforming zone comprises a second aromatization catalyst comprising a second transition metal and second catalyst support;

(B) performing step (A) for a time period sufficient to form a spent first aromatization catalyst in the outer reforming zone;

(C) introducing a catalyst poisoning agent (or catalyst deactivating agent) agent into the radial flow reactor and contacting at least a portion of the spent first aromatization catalyst in the outer reforming zone (to partially or completely deactivate the portion of the spent first aromatization catalyst); and (D) introducing a second hydrocarbon feed into the radial flow reactor comprising the catalyst bed, and contacting the second hydrocarbon feed with the catalyst bed under second reforming conditions to produce a second aromatic product.

Aspect 3. The method of aspect 1 or 2, wherein the hydrocarbon feed, the first hydrocarbon feed, and the second hydrocarbon feed, independently, comprise non-aromatic hydrocarbons, comprise $C_6$-$C_9$ alkanes and/or cycloalkanes, or comprise $C_6$-$C_8$ alkanes and/or cycloalkanes.

Aspect 4. The method of any one of the preceding aspects, wherein the hydrocarbon feed, the first hydrocarbon feed, and the second hydrocarbon feed, independently, comprise hexane, heptane, or a combination thereof.

Aspect 5. The method of any one of the preceding aspects, wherein the aromatic product, the first aromatic product, and the second aromatic product, independently, comprise benzene, toluene, or a combination thereof.

Aspect 6. The method of any one of the preceding aspects, wherein the reforming conditions, the first reforming conditions, and the second reforming conditions, independently, comprise a reforming temperature in any reforming temperature range disclosed herein, for example, from about 350° C. to about 600° C., or from about 400° C. to about 600° C.

Aspect 7. The method of any one of the preceding aspects, wherein the reforming conditions, the first reforming conditions, and the second reforming conditions, independently, comprise a reforming pressure in any reforming pressure range disclosed herein, for example, from about 20 psig (138 kPag) to about 100 psig (689 kPag).

Aspect 8. The method of any one of the preceding aspects, wherein the first catalyst support and the second catalyst support, independently, comprise a zeolite, an amorphous inorganic oxide, or any combination thereof.

Aspect 9. The method of any one of the preceding aspects, wherein the first catalyst support and the second catalyst support, independently, comprise an L-zeolite, a Y-zeolite, a mordenite, an omega zeolite, and/or a beta zeolite.

Aspect 10. The method of any one of the preceding aspects, wherein the first catalyst support and the second catalyst support, independently, comprise a potassium L-zeolite or a barium ion-exchanged L-zeolite.

Aspect 11. The method of any one of the preceding aspects, wherein the first catalyst support and the second catalyst support, independently, comprise a binder comprising alumina, silica, a mixed oxide thereof, or a mixture thereof.

Aspect 12. The method of any one of the preceding aspects, wherein the first catalyst support and the second catalyst support (or the respective catalyst), independently, comprise any weight percentage of binder disclosed herein, e.g., from about 3 wt. % to about 35 wt. %, or from about 5 wt. % to about 30 wt. % binder, based on the total weight of the support (or the catalyst).

Aspect 13. The method of any one of the preceding aspects, wherein the first catalyst support and the second catalyst support, independently, comprise a silica-bound KL-zeolite.

Aspect 14. The method of any one of the preceding aspects, wherein the first transition metal and the second transition metal, independently, comprise a Group 7-11 transition metal, or a Group 8-11 transition metal.

Aspect 15. The method of any one of the preceding aspects, wherein the first transition metal and the second transition metal, independently, comprise platinum, rhenium, tin, iron, gold, or combinations thereof.

Aspect 16. The method of any one of the preceding aspects, wherein the first transition metal and the second transition metal comprise platinum.

Aspect 17. The method of any one of the preceding aspects, wherein the first aromatization catalyst, the second aromatization catalyst, and the spent first aromatization catalyst, independently, comprise any weight percentage range of (first or second) transition metal disclosed herein, for example, from about 0.1 wt. % to about 10 wt. %, or from about 0.3 wt. % to about 5 wt. %, transition metal.

Aspect 18. The method of any one of the preceding aspects, wherein the first aromatization catalyst, the second aromatization catalyst, and the spent first aromatization catalyst, independently, comprise any weight percentage range of platinum disclosed herein, for example, from about 0.1 wt. % to about 10 wt. %, or from about 0.5 wt. % to about 2 wt. %, platinum.

Aspect 19. The method of any one of the preceding aspects, wherein the first aromatization catalyst, the second aromatization catalyst, and the spent first aromatization catalyst, independently, comprise platinum on a L-zeolite.

Aspect 20. The method of any one of the preceding aspects, wherein the first aromatization catalyst, the second aromatization catalyst, and the spent first aromatization catalyst, independently, comprise platinum on a KL-zeolite.

Aspect 21. The method of any one of the preceding aspects, wherein the first aromatization catalyst, the second aromatization catalyst, and the spent first aromatization catalyst, independently, comprise platinum on a silica-bound KL-zeolite.

Aspect 22. The method of any one of the preceding aspects, wherein the first aromatization catalyst, the second aromatization catalyst, and the spent first aromatization catalyst further comprise chlorine and fluorine.

Aspect 23. The method of any one of the preceding aspects, wherein the first aromatization catalyst, the second aromatization catalyst, and the spent first aromatization catalyst, independently, comprise any amount of chlorine and/or any amount of fluorine disclosed herein, for example, from about 0.01 wt. % to about 5 wt. %, or from about 0.3 to about 1.3 wt. % fluorine, and/or from about 0.01 wt. % to about 5 wt. %, or from about 0.3 to about 1.3 wt. % chlorine.

Aspect 24. The method of any one of the preceding aspects, wherein the first aromatization catalyst, the second aromatization catalyst, and the spent first aromatization catalyst, independently, comprise any molar ratio of fluorine:chlorine disclosed herein, for example, from about 0.2:1 to about 4:1.

Aspect 25. The method of any one of the preceding aspects, wherein a weight ratio (or volume ratio) of catalyst in the outer reforming zone to the inner reforming zone is in any range of outer:inner disclosed herein, for example, from about 10:1 to about 1:10, or from about 5:1 to about 1:5.

Aspect 26. The method of any one of the preceding aspects, wherein the catalyst poisoning agent comprises a material configured to bind to the transition metal (for example, platinum) such that the transition metal does not catalyze an aromatization reaction and/or does not catalyze a cracking reaction.

Aspect 27. The method of any one of the preceding aspects, wherein the catalyst poisoning agent comprises a material that is a gas throughout any range of temperatures disclosed herein, for example, a gas throughout the temperature range of 200° C. to 800° C., or a gas throughout the temperature range of 300° C. to 700° C.

Aspect 28. The method of any one of the preceding aspects, wherein the catalyst poisoning agent comprises a heavy hydrocarbon (e.g., anthracene), a sulfur-containing compound (e.g., $H_2S$, a thiophene, a mercaptan), a phosphorus-containing compound (e.g., a phosphate, a phosphine), an oxygen-containing compound (e.g., acetaldehyde), a bromine-containing compound (e.g., a brominated hydrocarbon), an iodine-containing compound (e.g., an iodinated hydrocarbon), an organometallic lead compound (e.g., tetraethyl lead), an organometallic arsenic compound (e.g., trimethylarsine), or any combination thereof.

Aspect 29. The method of any one of the preceding aspects, wherein the catalyst poisoning agent is introduced at a molar ratio of moles of the catalyst poisoning agent to moles of transition metal (in the spent first aromatization catalyst) in any range disclosed herein, for example, from about 0.01:1 to about 1:1, from about 0.01:1 to about 0.5:1, or from about 0.1:1 to about 0.75:1.

Aspect 30. The method of any one of the preceding aspects, wherein the amount of carbon on the spent first aromatization catalyst is in any range of weight percentages of carbon disclosed herein, for example, from about 1 to 10 wt. %, or from about 1.5 to about 7 wt. % carbon.

Aspect 31. The method of any one of the preceding aspects, wherein the amount of carbon on the first aromatization catalyst and second aromatization catalyst, independently, is in any range of weight percentages of carbon disclosed herein, for example, less than about 0.9 wt. %, less than about 0.5 wt. %, from about 0.01 wt. % to about 0.9 wt. %, from about 0.01 wt. % to about 0.5 wt. %, or from about 0.02 wt. % to about 0.5 wt. % carbon.

Aspect 32. The method of any one of the preceding aspects, wherein the temperature of the hydrocarbon feed, the first hydrocarbon feed, and the second hydrocarbon feed decreases from the outer reforming zone to the inner reforming zone.

Aspect 33. The method of any one of the preceding aspects, wherein the activity (e.g., aromatics yield) of the second aromatization catalyst is greater than that of the spent first aromatization catalyst, under the same test conditions.

Aspect 34. The method of any one of the preceding aspects, wherein an aromatics selectivity of the second aromatization catalyst is greater than that of the spent first aromatization catalyst, under the same test conditions.

Aspect 35. The method of any one of the preceding aspects, wherein an aromatics yield of the spent first aromatization catalyst after contact with the catalyst poisoning agent is less than 10 wt. %, for example, less than 5 wt. %, or effectively zero (no catalytic activity).

Aspect 36. The method of any one of the preceding aspects, wherein a yield of the aromatic product in step (c) is greater than a yield of an aromatic product produced after step (a) and before step (b), and a yield of the second aromatic product in step (D) is greater than a yield of the first aromatic product produced after step (B) and before step (C).

Aspect 37. The method of any one of the preceding aspects, wherein an aromatics selectivity of the aromatic product in step (c) is greater than an aromatics selectivity of an aromatic product produced after step (a) and before step (b), and an aromatics selectivity of the second aromatic product in step (D) is greater than an aromatics selectivity of the first aromatic product produced after step (B) and before step (C).

Aspect 38. The method of any one of the preceding aspects, wherein the method further comprises an inert gas purging step after the catalyst poisoning step, the inert gas purging step comprising introducing an inert gas stream into the radial flow reactor and contacting the catalyst bed, wherein the inert gas stream comprises (or consists essentially of, or consists of) any inert gas disclosed herein, for example, nitrogen.

Aspect 39. An aromatization reactor vessel comprising:
(i) a reactor wall;
(ii) a catalyst bed positioned within the reactor vessel;
(iii) an outer annulus positioned between the reactor wall and an outer particle barrier, the outer particle barrier and the outer annulus surrounding the catalyst bed;
(iv) a reactor inlet for a feed stream; and
(v) a reactor outlet connected to a center pipe, the center pipe positioned in the reactor vessel and surrounded by the catalyst bed;
wherein the catalyst bed comprises an outer (first) reforming zone and an inner (second) reforming zone, the outer reforming zone comprising a deactivated first aromatization catalyst comprising a first transition metal and a first catalyst support, and the inner reforming zone comprising a second aromatization catalyst comprising a second transition metal and a second catalyst support;
wherein a flow path for the feed stream begins at the reactor inlet; continues to the outer annulus; through the outer particle barrier, the outer reforming zone, and the inner reforming zone; into the center pipe; and to the reactor outlet.

Aspect 40. The reactor vessel of aspect 39, wherein the reactor vessel comprises stainless steel.

Aspect 41. The reactor vessel of aspect 39 or 40, wherein the outer annulus comprises flow-affecting elements (for example, scallops, adjacent to the reactor wall) in the flow path to promote flow through the catalyst bed.

Aspect 42. The reactor vessel of any one of aspects 39-41, wherein the reactor vessel is configured for an operating pressure in any suitable range or in any range disclosed herein, for example, at least 20 psig (138 kPag), at least 30 psig (207 kPag), or from about 20 psig (138 kPag) to about 100 psig (689 kPag).

Aspect 43. The reactor vessel of any one of aspects 39-42, wherein the center pipe and the catalyst bed are positioned concentrically.

Aspect 44. The reactor vessel of any one of aspects 39-43, wherein the center pipe comprises a screen or mesh section within the reactor vessel.

Aspect 45. The reactor vessel of any one of aspects 39-44, wherein the center pipe comprises a coating/layer comprising any suitable metal or any metal disclosed herein (for example, tin) that provides resistance to carburization and metal dusting.

Aspect 46. The reactor vessel of any one of aspects 39-45, wherein the reactor vessel comprises a coating/layer comprising any suitable metal or any metal disclosed herein (for example, tin) that provides resistance to carburization and metal dusting.

Aspect 47. The reactor vessel of any one of aspects 39-46, wherein the reactor vessel is configured for decreasing temperature from the outer annulus to the center pipe (or from the outer reforming zone to the inner reforming zone).

Aspect 48. The reactor vessel of any one of aspects 39-47, wherein the reactor vessel is configured as a radial flow reactor.

Aspect 49. The reactor vessel of any one of aspects 39-48, wherein the reactor vessel is configured for a catalytic conversion of a non-aromatic hydrocarbon to an aromatic hydrocarbon (for example, benzene, toluene, or xylenes).

Aspect 50. The reactor vessel of any one of aspects 39-49, wherein the reactor vessel further comprises a top cover plate positioned at the top of the center pipe and the catalyst bed.

Aspect 51. The reactor vessel of any one of aspects 39-50, wherein the reactor vessel further comprises an integrated heat exchange system around at least a portion of the reactor vessel for controlling temperature within the reactor vessel.

Aspect 52. The reactor vessel of any one of aspects 39-51, wherein the first catalyst support and the second catalyst support, independently, comprise a zeolite, an amorphous inorganic oxide, or any combination thereof.

Aspect 53. The reactor vessel of any one of aspects 39-52, wherein the first catalyst support and the second catalyst support, independently, comprise an L-zeolite, a Y-zeolite, a mordenite, an omega zeolite, and/or a beta zeolite.

Aspect 54. The reactor vessel of any one of aspects 39-53, wherein the first catalyst support and the second catalyst support, independently, comprise a potassium L-zeolite or a barium ion-exchanged L-zeolite.

Aspect 55. The reactor vessel of any one of aspects 39-54, wherein the first catalyst support and the second catalyst support, independently, comprise a binder comprising alumina, silica, a mixed oxide thereof, or a mixture thereof.

Aspect 56. The reactor vessel of any one of aspects 39-55, wherein the first catalyst support and the second catalyst support, independently, comprise a silica-bound KL-zeolite.

Aspect 57. The reactor vessel of any one of aspects 39-56, wherein the first transition metal and the second transition metal, independently, comprise a Group 7-11 transition metal, or a Group 8-11 transition metal.

Aspect 58. The reactor vessel of any one of aspects 39-57, wherein the first transition metal and the second transition metal, independently, comprise platinum, rhenium, tin, iron, gold, or combinations thereof.

Aspect 59. The reactor vessel of any one of aspects 39-58, wherein the first transition metal and the second transition metal comprise platinum.

Aspect 60. The reactor vessel of any one of aspects 39-59, wherein the deactivated first aromatization catalyst and the second aromatization catalyst, independently, comprise platinum on a L-zeolite.

Aspect 61. The reactor vessel of any one of aspects 39-60, wherein the deactivated first aromatization catalyst and the second aromatization catalyst, independently, comprise platinum on a KL-zeolite.

Aspect 62. The reactor vessel of any one of aspects 39-61, wherein the deactivated first aromatization catalyst and the second aromatization catalyst, independently, comprise platinum on a silica-bound KL-zeolite.

Aspect 63. The reactor vessel of any one of aspects 39-62, wherein the deactivated first aromatization catalyst and the second aromatization catalyst further comprise chlorine and fluorine.

Aspect 64. The reactor vessel of any one of aspects 39-63, wherein a weight ratio (or volume ratio) of catalyst in the outer reforming zone to the inner reforming zone is in any range of outer:inner disclosed herein, for example, from about 10:1 to about 1:10, or from about 5:1 to about 1:5.

Aspect 65. The reactor vessel of any one of aspects 39-64, wherein the deactivated first aromatization catalyst is configured to not catalyze an aromatization reaction and/or is configured to not catalyze a cracking reaction.

Aspect 66. The reactor vessel of any one of aspects 39-65, wherein the amount of carbon on the deactivated first aromatization catalyst is in any range of weight percentages of carbon disclosed herein, for example, from about 1 to 10 wt. %, or from about 1.5 to about 7 wt. % carbon.

Aspect 67. The reactor vessel of any one of aspects 39-66, wherein the amount of carbon on the second aromatization catalyst is in any range of weight percentages of carbon disclosed herein, for example, less than about 0.9 wt. %, less than about 0.5 wt. %, from about 0.01 wt. % to about 0.9 wt. %, from about 0.01 wt. % to about 0.5 wt. %, or from about 0.02 wt. % to about 0.5 wt. % carbon.

Aspect 68. The reactor vessel of any one of aspects 39-67, wherein an aromatics yield of the deactivated first aromatization catalyst is less than 10 wt. %, for example, less than 5 wt. %, or effectively zero (no catalytic activity).

Aspect 69. The reactor vessel of any one of aspects 39-68, wherein the reactor vessel is configured for an aromatics yield at the reactor outlet that is greater than that obtained using a spent first aromatization catalyst, instead of the deactivated first aromatization catalyst, in the outer reforming zone.

Aspect 70. The reactor vessel of any one of aspects 39-69, wherein the reactor vessel is configured for an aromatics selectivity at the reactor outlet that is greater than that obtained using a spent first aromatization catalyst, instead of the deactivated first aromatization catalyst, in the outer reforming zone.

Aspect 71. An aromatization reactor system comprising two or more aromatization reactor vessels, at least one of which is the reactor vessel of any one of aspects 39-70.

Aspect 72. The system of aspect 71, wherein the system comprises any suitable number of reactor vessels in series or any number of reactor vessels in series disclosed herein, for example, from 2 to 8 vessels in series, or 6 vessels in series.

Aspect 73. The system of aspect 72, wherein the system further comprises a furnace before each reactor vessel, each furnace configured to heat the feed stream (or a reactor effluent of the previous reactor vessel) to a reactor vessel operating temperature, independently, of from about 350° C. to about 600° C.

We claim:

1. A reforming method comprising:
   (A) introducing a first hydrocarbon feed into a radial flow reactor comprising a catalyst bed, and contacting the first hydrocarbon feed with the catalyst bed under first reforming conditions to produce a first aromatic product; wherein:
   the catalyst bed comprises an outer reforming zone and an inner reforming zone;
   the outer reforming zone comprises a first aromatization catalyst comprising a first transition metal and a first catalyst support; and
   the inner reforming zone comprises a second aromatization catalyst comprising a second transition metal and a second catalyst support;
   (B) performing step (A) for a time period sufficient to form a spent first aromatization catalyst in the outer reforming zone;
   (C) introducing a catalyst poisoning agent into the radial flow reactor and contacting at least a portion of the spent first aromatization catalyst to form a poisoned aromatization catalyst in the outer reforming zone; and
   (D) introducing a second hydrocarbon feed into the radial flow reactor comprising the catalyst bed, and contacting the second hydrocarbon feed with the catalyst bed under second reforming conditions to produce a second aromatic product; wherein:
   the spent first aromatization catalyst comprises from about 1 wt. % to about 10 wt. % carbon;
   the poisoned aromatization catalyst has an aromatics yield of less than 10 wt. %; and
   the catalyst poisoning agent comprises a heavy hydrocarbon, a sulfur-containing compound, a phosphorus-containing compound, an oxygen-containing compound, a bromine-containing compound, an iodine-containing compound, an organometallic lead compound, an organometallic arsenic compound, or any combination thereof.

2. The method of claim 1, wherein:
   the first aromatization catalyst comprises from about 0.3 wt. % to about 5 wt. % of the first transition metal; and
   the second aromatization catalyst comprises from about 0.3 wt. % to about 5 wt. % of the second transition metal.

3. The method of claim 1, wherein:
   the first transition metal and the second transition metal comprise platinum;
   the first catalyst support and the second catalyst support comprise a KL-zeolite and a binder comprising alumina, silica, a mixed oxide thereof, or a mixture thereof; and
   the first aromatization catalyst and the second aromatization catalyst further comprise chlorine and fluorine.

4. The method of claim 1, wherein:
   the first aromatic product and the second aromatic product, independently, comprise benzene, toluene, or a combination thereof; and
   the first reforming conditions and the second reforming conditions, independently, comprise a reforming temperature in a range from about 350° C. to about 600° C.

5. The method of claim 1, wherein a weight ratio of catalyst in the outer reforming zone to the inner reforming zone is in a range from about 1:1.5 to about 1:5.

6. The method of claim 3, wherein the first aromatization catalyst and the second aromatization catalyst, independently, comprise from about 0.5 wt. % to about 2 wt. % of platinum.

7. The method of claim 1, wherein the catalyst poisoning agent is introduced at a molar ratio, based on moles of the catalyst poisoning agent to moles of the first transition metal in the spent first aromatization catalyst, in a range from about 0.1:1 to about 0.75:1.

8. The method of claim 7, wherein:
   the first transition metal and the second transition metal comprise platinum;
   the first catalyst support and the second catalyst support comprise a KL-zeolite and a binder comprising alumina, silica, a mixed oxide thereof, or a mixture thereof; and
   the first aromatization catalyst and the second aromatization catalyst further comprise chlorine and fluorine.

9. The method of claim 1, wherein:
   the aromatics yield of the second aromatization catalyst is greater than that of the spent first aromatization catalyst, under the same test conditions; and
   the aromatics selectivity of the second aromatization catalyst is greater than that of the spent first aromatization catalyst, under the same test conditions.

10. The method of claim 1, wherein an aromatics yield of the second aromatic product in step (D) is greater than a yield of the first aromatic product produced after step (B) and before step (C).

11. The method of claim 1, wherein an aromatics selectivity of the second aromatic product in step (D) is greater than an aromatics selectivity of the first aromatic product produced after step (B) and before step (C).

12. A reforming method comprising:
(a) providing a radial flow reactor comprising a catalyst bed, the catalyst bed comprising an outer reforming zone and an inner reforming zone; wherein:
the outer reforming zone comprises a spent first aromatization catalyst comprising a first transition metal and a first catalyst support; and
the inner reforming zone comprises a second aromatization catalyst comprising a second transition metal and a second catalyst support;
(b) introducing a catalyst poisoning agent into the radial flow reactor and contacting at least a portion of the spent first aromatization catalyst to form a poisoned aromatization catalyst in the outer reforming zone; and
(c) introducing a hydrocarbon feed into the radial flow reactor comprising the catalyst bed, and contacting the hydrocarbon feed with the catalyst bed under reforming conditions to produce an aromatic product; wherein:
the spent first aromatization catalyst comprises from about 1 wt. % to about 10 wt. % carbon;
the poisoned aromatization catalyst has an aromatics yield of less than 10 wt. %; and
the catalyst poisoning agent comprises a heavy hydrocarbon, a sulfur-containing compound, a phosphorus-containing compound, an oxygen-containing compound, a bromine-containing compound, an iodine-containing compound, an organometallic lead compound, an organometallic arsenic compound, or any combination thereof.

13. The method of claim 12, wherein:
an aromatics yield of the aromatic product in step (c) is greater than a yield of an aromatic product produced after step (a) and before step (b); and
an aromatics selectivity of the aromatic product in step (c) is greater than an aromatics selectivity of an aromatic product produced after step (a) and before step (b).

14. The method of claim 13, wherein:
the first transition metal and the second transition metal comprise platinum;
the first catalyst support and the second catalyst support comprise a KL-zeolite and a binder comprising alumina, silica, a mixed oxide thereof, or a mixture thereof; and
the spent first aromatization catalyst and the second aromatization catalyst further comprise chlorine and fluorine.

15. The method of claim 14, wherein:
the spent first aromatization catalyst and the second aromatization catalyst, independently, comprise from about 0.3 wt. % to about 5 wt. % of platinum; and
the aromatic product comprises benzene, toluene, or a combination thereof.

16. The method of claim 15, wherein the spent first aromatization catalyst comprises from about 1.5 wt. % to about 7 wt. % carbon.

17. A reforming method comprising:
(A) introducing a first hydrocarbon feed into a radial flow reactor comprising a catalyst bed, and contacting the first hydrocarbon feed with the catalyst bed under first reforming conditions to produce a first aromatic product; wherein:
the catalyst bed comprises an outer reforming zone and an inner reforming zone;
the outer reforming zone comprises a first aromatization catalyst comprising a first transition metal and a first catalyst support; and
the inner reforming zone comprises a second aromatization catalyst comprising a second transition metal and a second catalyst support;
(B) performing step (A) for a time period sufficient to form a spent first aromatization catalyst in the outer reforming zone;
(C) introducing a catalyst poisoning agent into the radial flow reactor and contacting at least a portion of the spent first aromatization catalyst to form a poisoned aromatization catalyst in the outer reforming zone; and
(D) introducing a second hydrocarbon feed into the radial flow reactor comprising the catalyst bed, and contacting the second hydrocarbon feed with the catalyst bed under second reforming conditions to produce a second aromatic product; wherein:
the spent first aromatization catalyst comprises from about 1 wt. % to about 10 wt. % carbon;
the poisoned aromatization catalyst has an aromatics yield of less than 10 wt. %;
the catalyst poisoning agent comprises a heavy hydrocarbon, a sulfur-containing compound, a phosphorus-containing compound, an oxygen-containing compound, a bromine-containing compound, an iodine-containing compound, an organometallic lead compound, an organometallic arsenic compound, or any combination thereof;
an aromatics yield of the second aromatic product in step (D) is greater than a yield of the first aromatic product produced after step (B) and before step (C); and
an aromatics selectivity of the second aromatic product in step (D) is greater than an aromatics selectivity of the first aromatic product produced after step (B) and before step (C).

18. The method of claim 17, wherein the first aromatization catalyst and the second aromatization catalyst, independently, comprise from about 0.5 wt. % to about 2 wt. % of platinum.

19. The method of claim 18, wherein:
the first aromatic product and the second aromatic product, independently, comprise benzene, toluene, or a combination thereof; and
the first catalyst support and the second catalyst support comprise a silica-bound KL-zeolite.

20. The method of claim 17, wherein:
a weight ratio of catalyst in the outer reforming zone to the inner reforming zone is in a range from about 1:1.5 to about 1:5; and
the catalyst poisoning agent is introduced at a molar ratio, based on moles of the catalyst poisoning agent to moles of the first transition metal in the spent first aromatization catalyst, in a range from about 0.1:1 to about 0.75:1.

* * * * *